United States Patent
Stout et al.

(10) Patent No.: US 8,357,119 B2
(45) Date of Patent: Jan. 22, 2013

(54) CATHETER ASSEMBLY AND PIERCED SEPTUM VALVE

(75) Inventors: Marty L. Stout, South Jordan, UT (US); Jonathan K. Burkholz, Salt Lake City, UT (US); Douglas Anjewierden, Salt Lake City, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 13/042,114

(22) Filed: Mar. 7, 2011

(65) Prior Publication Data

US 2012/0016302 A1    Jan. 19, 2012

Related U.S. Application Data

(60) Provisional application No. 61/364,576, filed on Jul. 15, 2010, provisional application No. 61/365,391, filed on Jul. 19, 2010.

(51) Int. Cl.
*A61M 5/36* (2006.01)

(52) U.S. Cl. ............. 604/122; 604/167.01; 604/236; 604/533; 604/537

(58) Field of Classification Search .......... 604/523, 604/533–535, 537, 539, 236, 167.01–167.04, 604/167.06, 256, 264, 122
See application file for complete search history.

(56) References Cited

U.S. PATENT DOCUMENTS

| | | | |
|---|---|---|---|
| 4,043,346 A * | 8/1977 | Mobley et al. ............... | 604/107 |
| 4,387,879 A | 6/1983 | Tauschinski | |
| 4,449,693 A | 5/1984 | Gereg | |
| 4,758,225 A | 7/1988 | Cox et al. | |
| 4,842,591 A | 6/1989 | Luther | |
| 4,874,377 A | 10/1989 | Newgard et al. | |
| 4,917,668 A | 4/1990 | Haindl | |
| 4,935,010 A | 6/1990 | Cox et al. | |
| 5,041,097 A | 8/1991 | Johnson | |
| 5,053,014 A | 10/1991 | Van Heugten | |
| 5,062,836 A | 11/1991 | Wendell | |
| 5,064,416 A | 11/1991 | Newgard et al. | |
| 5,084,023 A | 1/1992 | Lemieux | |
| 5,085,645 A | 2/1992 | Purdy et al. | |
| 5,108,374 A | 4/1992 | Lemieux | |
| 5,127,905 A | 7/1992 | Lemieux | |
| 5,154,703 A | 10/1992 | Bonaldo | |
| 5,156,596 A | 10/1992 | Balbierz et al. | |

(Continued)

FOREIGN PATENT DOCUMENTS

| | | |
|---|---|---|
| CA | 2133053 A1 | 3/1995 |
| WO | WO 99/34849 | 7/1999 |

(Continued)

OTHER PUBLICATIONS

Silva, Elson, Email Regarding "Respecting Hydrology Science and IP Rights—US Pat. Application 20110130728," pp. 1-6, Jun. 2, 2011.

*Primary Examiner* — Quynh-Nhu H Vu

(74) *Attorney, Agent, or Firm* — Jeanne Lukasavage; Craig Metcalf; Kirton McConkie

(57) ABSTRACT

A septum activator is disclosed herein. The septum activator has an outer tubular body and an inner tubular body. The outer tubular body and the inner tubular body each have a plurality of openings therein. The inner tubular body has a first position relative to the outer tubular body and a second position relative to outer tubular body. In the first position, the plurality of openings of the inner tubular body do not overlap with the plurality of openings in the outer tubular body. In the second position, the plurality of openings of the inner tubular body overlap with the plurality of openings of the inner tubular body.

19 Claims, 16 Drawing Sheets

U.S. PATENT DOCUMENTS

| | | | |
|---|---|---|---|
| 5,234,410 A | 8/1993 | Graham et al. |
| 5,295,969 A | 3/1994 | Fischell et al. |
| 5,330,435 A | 7/1994 | Vaillancourt |
| 5,350,363 A | 9/1994 | Goode et al. |
| 5,352,205 A | 10/1994 | Dales et al. |
| 5,405,323 A | 4/1995 | Rogers et al. |
| 5,456,675 A | 10/1995 | Wolbring et al. |
| 5,487,728 A | 1/1996 | Vaillancourt |
| 5,520,666 A | 5/1996 | Choudhury et al. |
| 5,549,566 A | 8/1996 | Elias et al. |
| 5,549,577 A | 8/1996 | Siegel et al. |
| 5,575,769 A | 11/1996 | Vaillancourt |
| 5,613,663 A | 3/1997 | Schmidt et al. |
| 5,651,772 A | 7/1997 | Arnett |
| 5,657,963 A | 8/1997 | Hinchliffe et al. |
| 5,697,915 A | 12/1997 | Lynn |
| 5,738,144 A | 4/1998 | Rogers |
| 5,749,861 A | 5/1998 | Guala et al. |
| 5,806,831 A | 9/1998 | Paradis |
| 5,817,069 A | 10/1998 | Arnett |
| 5,911,710 A | 6/1999 | Barry et al. |
| 5,954,698 A | 9/1999 | Pike |
| 5,967,490 A | 10/1999 | Pike |
| 6,039,302 A | 3/2000 | Cote, Sr. et al. |
| 6,077,244 A | 6/2000 | Botich et al. |
| 6,117,108 A | 9/2000 | Woehr et al. |
| 6,171,287 B1 | 1/2001 | Lynn et al. |
| 6,273,869 B1 | 8/2001 | Vaillancourt |
| 6,485,473 B1 | 11/2002 | Lynn |
| 6,575,960 B2 | 6/2003 | Becker et al. |
| 6,595,981 B2 | 7/2003 | Huet |
| 6,699,221 B2 | 3/2004 | Vaillancourt |
| 6,740,063 B2 | 5/2004 | Lynn |
| 6,883,778 B1 | 4/2005 | Newton et al. |
| 7,008,404 B2 | 3/2006 | Nakajima |
| 7,347,839 B2 | 3/2008 | Hiejima |
| 7,396,346 B2 | 7/2008 | Nakajima |
| 7,470,254 B2 | 12/2008 | Basta et al. |
| 7,736,339 B2 | 6/2010 | Woehr et al. |
| 7,905,856 B2 * | 3/2011 | McGuckin et al. | 604/104 |
| 7,914,494 B2 | 3/2011 | Hiejima |
| 2007/0083162 A1 | 4/2007 | O'Reagan et al. |
| 2008/0039796 A1 | 2/2008 | Nakajima |
| 2008/0108944 A1 | 5/2008 | Woehr et al. |
| 2010/0204675 A1 | 8/2010 | Woehr et al. |

FOREIGN PATENT DOCUMENTS

| | | |
|---|---|---|
| WO | WO 2006/037638 A1 | 4/2006 |
| WO | WO 2009/114833 A1 | 9/2009 |

* cited by examiner

CATHETER ASSEMBLY AND PIERCED SEPTUM VALVE

RELATED APPLICATIONS

This application claims the benefit of U.S. Provisional Application No. 61/364,576 filed Jul. 15, 2010, entitled PIERCED SEPTUM BLOOD CONTROL VALVE WITH A FLOW RESTRICTOR AND A BLOOD VALVE FORMING A TERTIARY FLASHBACK CHAMBER, and U.S. Provisional Application No. 61/365,391 filed Jul. 19, 2010, entitled ACTUATOR FOR A PIERCED SEPTUM BLOOD CONTROL VALVE THAT PROVIDES A FLUSHING A TERTIARY FLASHBACK CHAMBER (APTURA ACTUATOR). This application claims priority to and incorporates by reference both of these provisional applications.

BACKGROUND

Catheters are commonly used for a variety of infusion therapies. For example, catheters are used for infusing fluids, such as normal saline solution, various medicaments, and total parenteral nutrition into a patient; withdrawing blood from a patient; or monitoring various parameters of the patient's vascular system. Catheters are typically coupled to a catheter adapter that supports catheter and provides for an attachment to IV tubing. Generally, following placement of the catheter into the vasculature of a patient, the catheter adapter may be coupled to a fluid source via a section of IV tubing to infuse fluids into the patient.

In order to verify proper placement of the catheter in the blood vessel, the clinician generally confirms that there is "flashback" of blood from the patient's vasculature into a flashback chamber of the catheter or catheter adapter. Once proper placement of the catheter is confirmed, the clinician must attach the catheter adapter to a section of IV tubing, or continue to manually occlude the vein to prevent undesirable exposure to blood. The process of coupling the catheter adapter to the section of IV tubing requires the clinician to awkwardly maintain pressure on the vein of the patient while simultaneously coupling the catheter adapter and the IV tubing. A common, yet undesirable practice is to permit blood to temporarily and freely flow from the catheter adapter while the clinician locates and couples the IV tubing to the catheter adapter. Another common practice is to attach the catheter adapter to the IV tubing prior to placing the catheter into the vein of the patient. While this method may prevent undesirable exposure to blood, positive pressure from the IV tubing into the catheter can does not permit desirable flashback and thus reduces a clinician's ability to confirm proper catheter placement.

Accordingly, there is a need in the art for a catheter assembly that permits controlled, desirable flashback without the risk of encountering undesirable exposure to blood. Such a catheter assembly is disclosed herein.

SUMMARY

In order to overcome the limitations discussed above, the present invention relates to a pierced septum valve that provide selective activation of fluid flow through the catheter assembly while minimizing or eliminating blood exposure. Furthermore, confirmation of catheter placement can be enhanced with an additional flash chamber that is created by including a seal around the exterior of the septum activator. The combination of the pierced septum valve and the seal about the septum activator can provide a longer flashback period in which clinicians can assure that a catheter is properly placed in a blood vessel of a patient. Additionally, the septum activator can provide selective openings therein that open during activation and close when the septum activator is in a deactivated position. When closed, the openings form a barrier surface of the additional flashback chamber. When open, the openings provided fluid pathways through the septum activator that can flush fluid contained in the additional flashback chamber about the septum activator.

In one aspect, a septum activator has an outer tubular body and an inner tubular body. The outer tubular body and the inner tubular body each have a plurality of openings therein. The inner tubular body has a first position relative to the outer tubular body and a second position relative to outer tubular body. In the first position, the plurality of openings of the inner tubular body does not overlap with the plurality of openings in the outer tubular body. In the second position, the plurality of openings of the inner tubular body overlaps with the plurality of openings of the inner tubular body.

Some implementations include one or more of the following aspects. The inner tubular body moves from the first position to the second position as the inner tubular body or outer tubular body is rotated about a longitudinal axis of the inner body. The inner tubular body may move from the first position to the second position as the inner tubular body or the outer tubular body is translated along a longitudinal axis of the inner body. The plurality of openings in the outer tubular body may include a plurality of opening in a proximal portion of the outer tubular body and a plurality of openings in a distal portion of the outer tubular body, and the plurality of openings in the inner tubular body may include a plurality of opening in a proximal portion of the inner tubular body and a plurality of openings in a distal portion of the inner tubular body. The inner tubular body and the outer tubular body may each have a tapered portion. A seal may be disposed on an outer surface of the septum activator. One or more vents may be disposed on the seal, the one or more vents having cross sectional areas less than or equal to 0.00003 inches$^2$. One or more interlocking features may be between the inner tubular body and the outer tubular body that retain the inner tubular body within the outer tubular body.

In another aspect, a catheter assembly includes a catheter adapter, a septum, and a septum activator. The catheter adapter has a lumen extending therethrough. The septum is disposed within the lumen. A septum activator is disposed within the lumen proximal the septum. The septum activator has an inner tubular body and an outer tubular body. The outer tubular body of the septum activator has a plurality of openings therein. The inner tubular body of the septum activator is disposed within the outer tubular body and having a plurality of openings therein. The inner tubular body has a first position relative to the outer tubular body and a second position relative to outer tubular body. In the first position, the plurality of openings of the inner tubular body does not overlap with the plurality of openings in the outer tubular body. In the second position, the plurality of openings of the inner tubular body overlaps the plurality of openings of the inner tubular body.

Some implementations include one or more of the following aspects. The inner tubular body may move from the first position to the second position as the inner tubular body or outer tubular body is rotated about a longitudinal axis of the inner body. The inner tubular body may move from the first position to the second position as the inner tubular body or the outer tubular body is translated along a longitudinal axis of the inner body. The plurality of openings in the outer tubular body may include a plurality of opening in a proximal portion of the outer tubular body and a plurality of openings in a distal portion of the outer tubular body. The plurality of openings in the inner tubular body may include a plurality of opening in a proximal portion of the inner tubular body and a plurality of openings in a distal portion of the inner tubular body. The inner tubular body and the outer tubular body may each have a tapered portion. A seal may be disposed between an outer surface of the septum activator and the catheter adapter, the seal sealing the portion of the septum activator distal the lumen from the portion of the septum activator proximal the lumen. One or more vents may be disposed on the seal, the one or more vents having cross sectional areas less than or equal to 0.00003 inches². One or more interlocking features may be between the inner tubular body and the outer tubular body that retain the inner tubular body within the outer tubular body. The volume exterior the septum activator may be between the septum and the seal form a flashback chamber. When the inner tubular body is in the second position, the inner tubular body and the outer tubular body form a fluid tight barrier may be between an inner lumen of the inner tubular body and the flashback chamber. One or more flow restrictors may be between the septum and an inner surface of the catheter adapter, the one or more flow restrictors having cross sectional areas greater than 0.00003 inches².

In another aspect, a catheter assembly includes a catheter adapter, a septum, and a septum activator. The catheter adapter has a lumen extending therethrough. The septum is disposed within the lumen. A septum activator is disposed within the lumen proximal the septum. The septum activator has an inner tubular body and an outer tubular body. The outer tubular body of the septum activator has a plurality of openings therein. The inner tubular body of the septum activator is disposed within the outer tubular body and having a plurality of openings therein. The inner tubular body has a first position relative to the outer tubular body and a second position relative to outer tubular body. In the first position, the plurality of openings of the inner tubular body does not overlap with the plurality of openings in the outer tubular body. In the second position, the plurality of openings of the inner tubular body overlaps the plurality of openings of the inner tubular body. An annular seal is disposed between an outer surface of the septum activator and an inner surface of the lumen, the seal being disposed about a proximal portion of the septum activator. One or more vents are disposed between the seal and the lumen of the body.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

DETAILED DESCRIPTION OF THE INVENTION

Embodiment of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1:
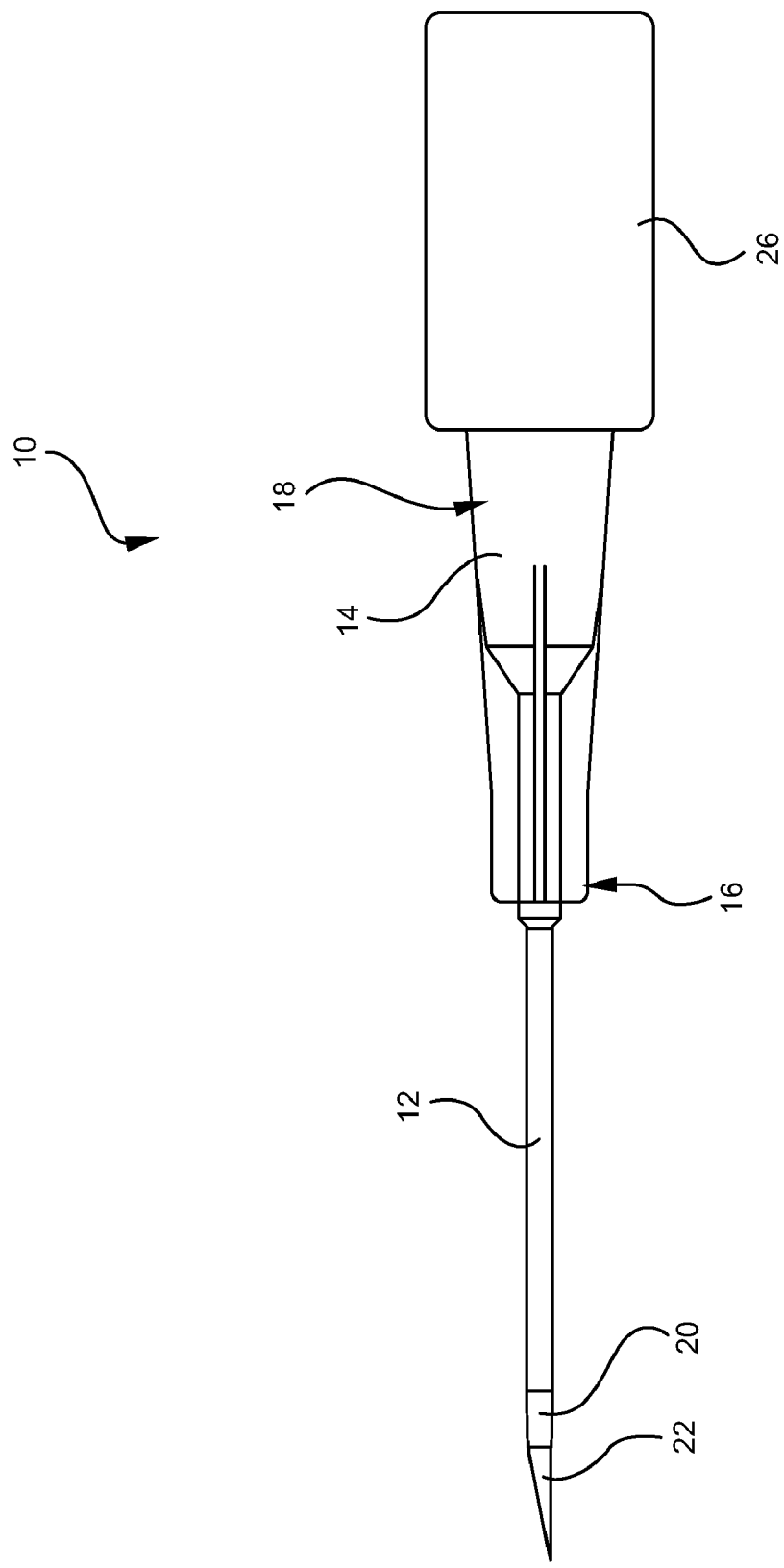
FIG. 1 is a perspective view of a catheter assembly, according to some embodiments.

Referring now to FIG. 1, a catheter assembly 10 is illustrated. The catheter assembly 10 generally includes a catheter 12 coupled to a distal end 16 of a catheter adapter 14. The catheter 12 and the catheter adapter 14 are integrally coupled such that an inner lumen of the catheter adapter 14 is in fluid communication with an inner lumen of the catheter 12. The catheter 12 generally comprises a biocompatible material having sufficient rigidity to withstand pressures associated with insertion of the catheter into a patient.

In some embodiments, as shown, the catheter 12 is an over-the-needle catheter that is made of a flexible or semi-flexible polymer material and which may be used in combination with a rigid introducer needle 22. The rigid introducer needle 22 enables the insertion of the non-rigid over-the-needle catheter into a patient. The introducer needle 22 can be coupled to a needle hub 26 that is selectively coupled to the proximal end 18 of the catheter adapter 14. The introducer needle 22 is typically inserted through the catheter 12 such that a tip of the needle 22 extends beyond the tapered tip 20 of the catheter 12. Insertion of the introducer needle 22 into the vein of the patient creates an opening in the vein through which the tapered tip 20 of the catheter 12 is inserted. The outer surface of the tapered tip 20 enables gradual insertion of the catheter 12 into the opening.

In other embodiments, the catheter 12 is not an over-the-needle catheter, but comprises a rigid, polymer material, such as vinyl. Rigid catheters can include a beveled cutting surface that is utilized to provide an opening in a patient to permit insertion of the catheter 12 into the vascular system of the patient. Accordingly, in some embodiments, the catheter 12 comprises a metallic material, such as titanium, stainless steel, nickel, molybdenum, surgical steel, and alloys thereof. Still, in other embodiments, surgically implanted catheters may also be used in combination with the present invention.

The catheter 12 can be a peripheral-type intravenous catheter that generally comprises a short or truncated catheter for insertion into a small peripheral vein. Such catheters generally comprise a diameter of about a 14-gauge catheter or smaller (on a Stubs scale), and is between about 13 mm to 52 mm in length. Peripheral intravenous catheters are typically designed for temporary placement. The short length of the catheter facilitates convenient placement of the catheter. In other embodiments, the catheter 12 is a midline or central catheter, which may be longer and used for more extended periods.

Figure 2:
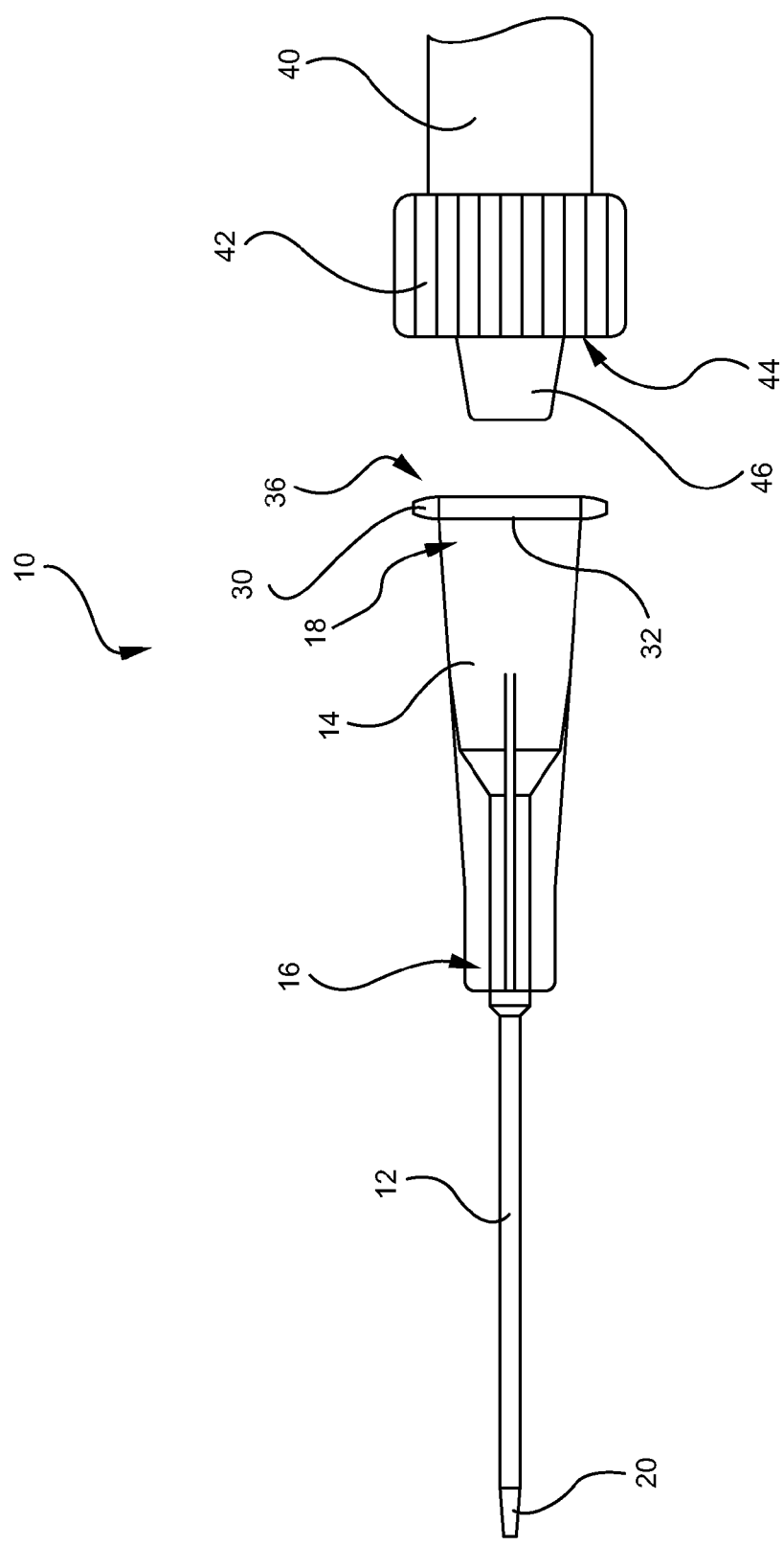
FIG. 2 is a perspective view of a catheter assembly following removal of an introducer needle, according to some embodiments.

Referring now to FIG. 2, once the catheter 12 is inserted into the vein of the patient, the introducer needle 22 is removed proximally from the catheter 12 to provide a fluid conduit through the interior lumen 36 of the catheter 12, which can be connected to a fluid source. In some embodiments, a portion of the catheter 12 and/or catheter adapter 14 is configured to be connected to a section of intravenous tubing 40 to further facilitate delivery of a fluid to or removal of a fluid from a patient. In some embodiments, a proximal end 18 of the catheter adapter 14 includes a flange 32. The flange 32 provides a positive surface that may be configured to enable coupling of an intravenous tubing 40 or patient conduit to the catheter assembly 10. In some embodiments, the flange 32 includes a set of threads 30. The threads 30 are generally provided and configured to compatibly receive a complementary set of threads 44 comprising a portion of a male luer or conduit coupler 42. The conduit coupler 42 is generally coupled to an end portion of the patient conduit 40 in a fluid-tight manner. In some embodiments, an inner portion of the conduit coupler 42 is extended outwardly to provide a probe member 46.

Figure 8:
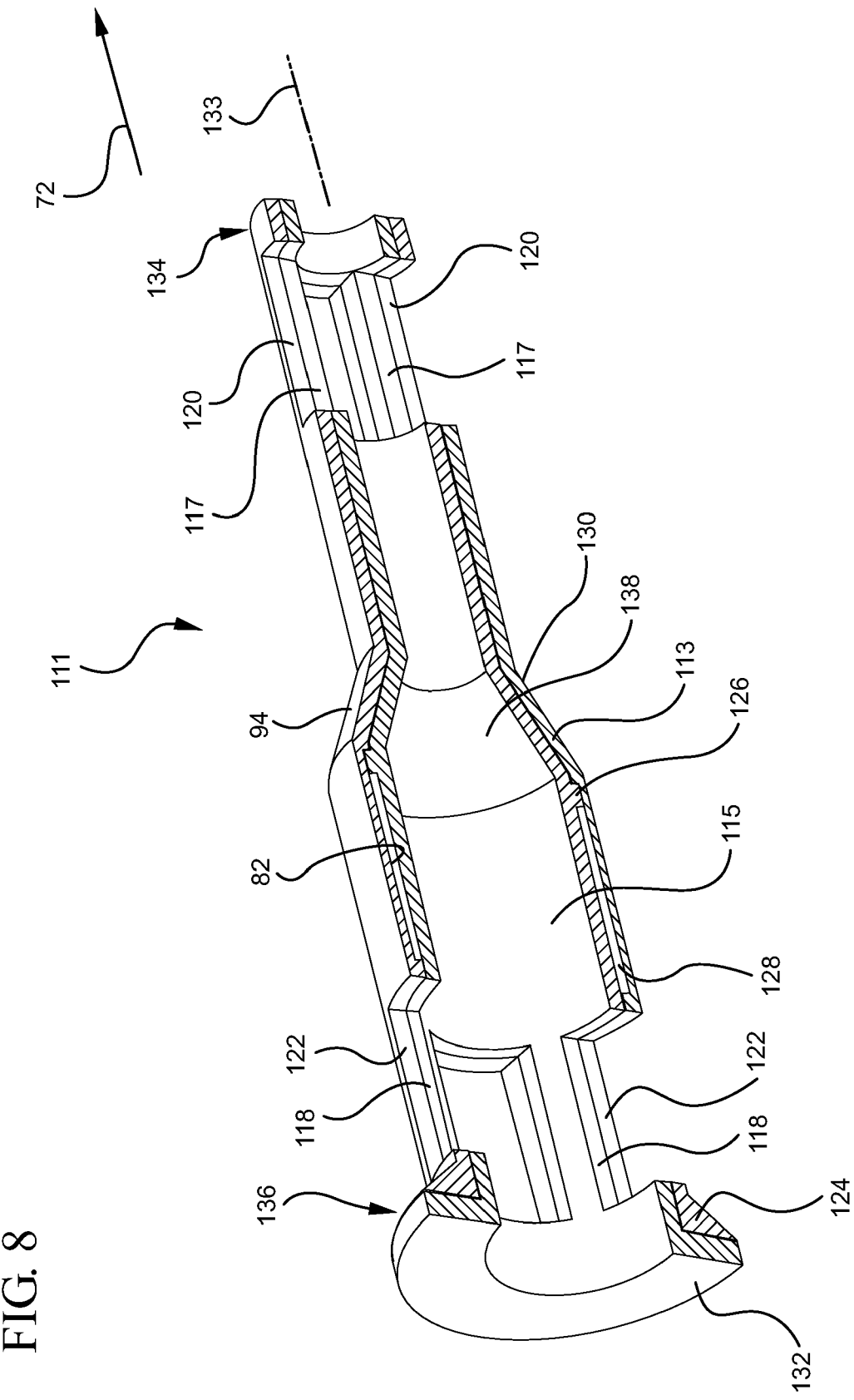
FIG. 8 is a perspective cross-sectioned view of the septum activator of FIG. 7 in a second position, according to some embodiments.

The probe member 46 can be compatibly inserted within a proximal end 18 of the catheter adapter 14 to activate the septum therein, thus opening a fluid path within the catheter adapter 14. In some configurations, following insertion of the probe member 46 into the proximal end 22 of the catheter adapter 14, the conduit coupler 42 is interlock with the coupler 42 and the flange 28 (via the sets of threads 30 and 44), such as by rotation. During the process of interlocking the coupler 42 and the flange 28, the probe member 46 is advanced into the lumen 36 of the catheter adapter 14 to an inserted position (as shown in FIGS. 8 and 12). As shown in FIGS. 8 and 12, as the intravenous tubing 40 is connected to the catheter adapter 14, the probe member 46 advances into the lumen 36 of the catheter adapter 14, forcing a septum activator therein to pierce through the septum 50. Piercing the septum 50 opens the septum and provides a fluid path through which fluids from the intravenous tubing 40 to flow through the pierced septum 50 and the catheter 12 into the patient. The process of piercing the septum 50 is described in detail below. As will be understood, prior to the insertion of the probing member 46, the inner lumen 36 of the catheter adapter 14 is sealed to avoid blood exposure through from flashback.

Figure 3:
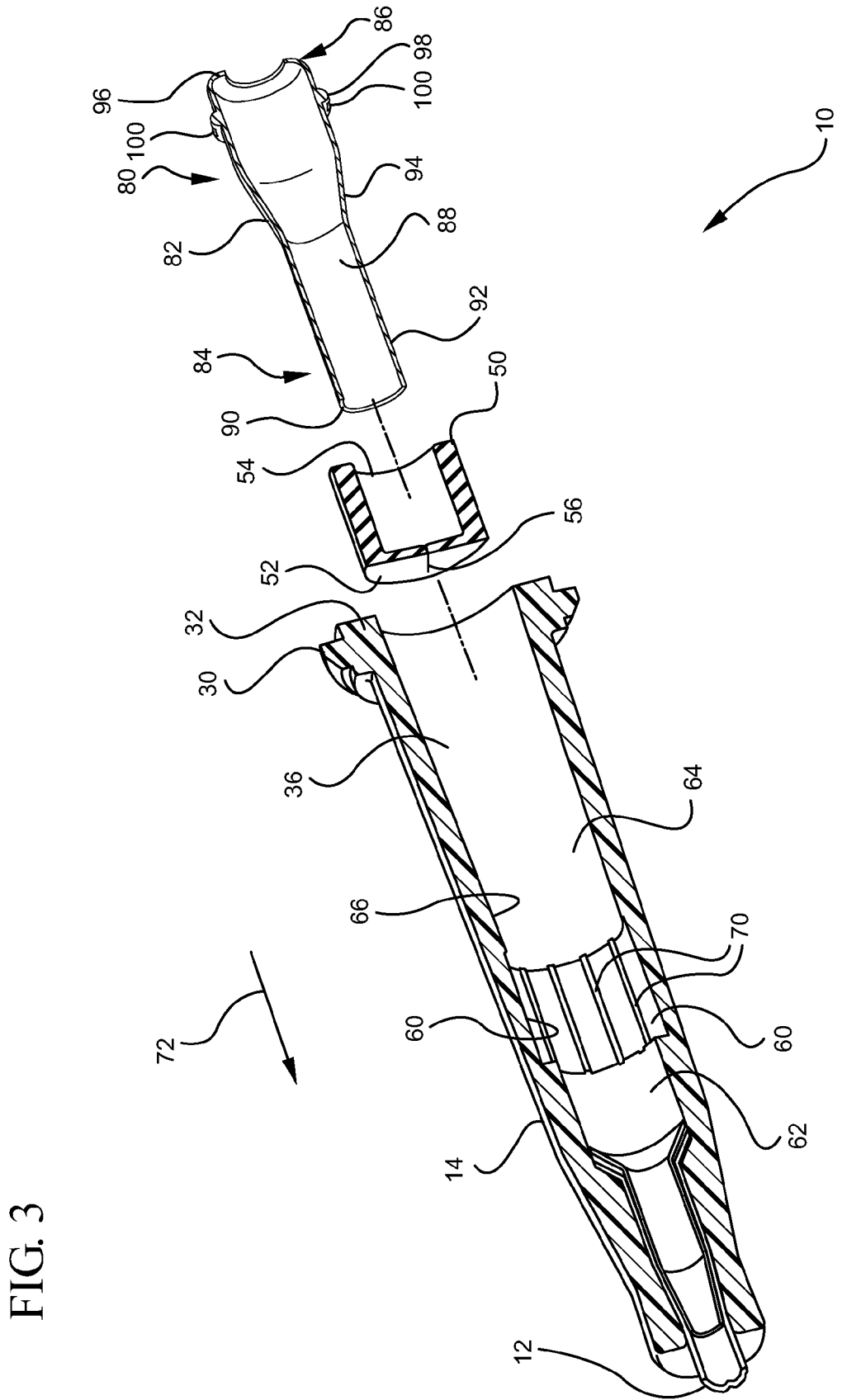
FIG. 3 is an exploded cross-sectioned view of a catheter assembly, according to some embodiments.
Figure 4:
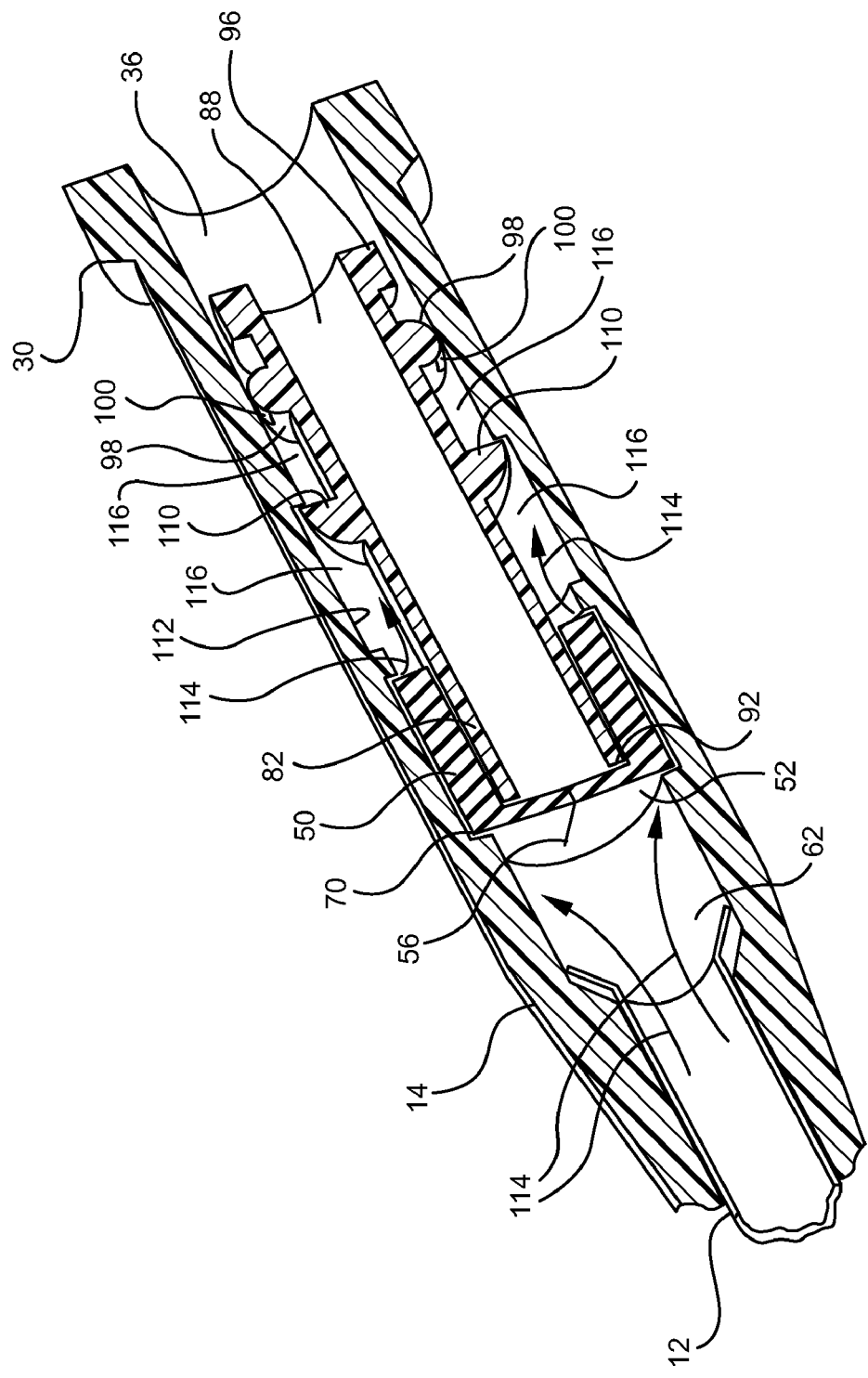
FIG. 4 is a perspective cross-sectioned view of a catheter assembly with a septum activator in a deactivated position, according to some embodiments.
Figure 6:
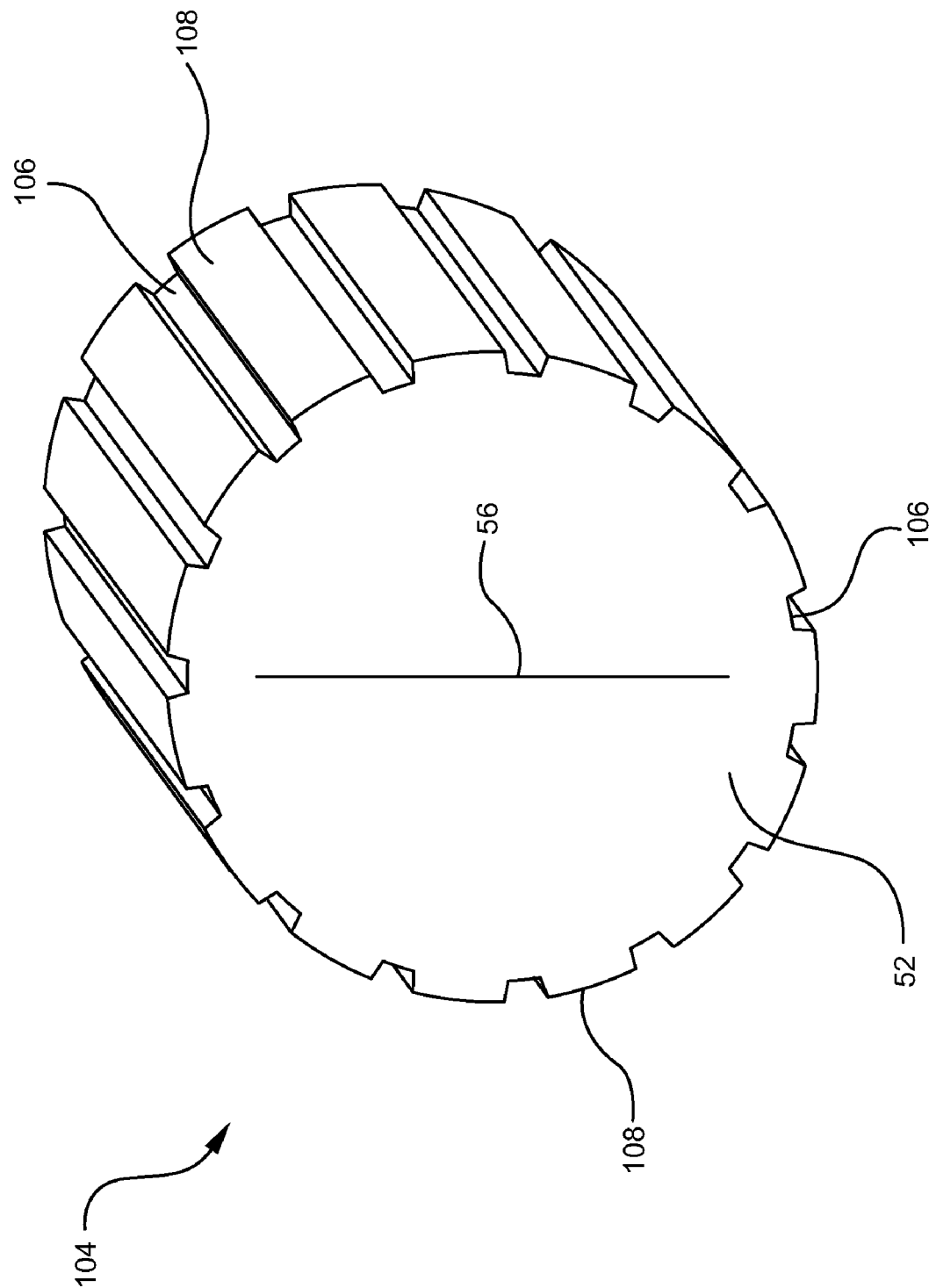
FIG. 6 is a perspective view of a septum, according to some embodiments.

Reference will now be made to FIGS. 3 and 4. FIG. 3 depicts an exploded, cross-sectional view of a catheter assembly 10. FIG. 4 depicts a cross-sectional view of an assembled catheter assembly 10. The septum activator 80 of FIG. 4 has an alternative structure to that of FIG. 3, as is explained below. These figures, along with FIG. 6, depict embodiments of pierced septum valves, which include a septum having a slit that is opened and closed by the advancement and retraction of a probe-like septum activator therethrough.

As shown, in some embodiments, a septum 50 is positioned within the inner lumen 36 of the catheter adapter 14 to control the flow of fluid therein. The septum 50 generally comprises a flexible or semi-flexible polymer plug having an outer diameter that is configured to compatibly sit within a groove or channel 60 formed on an inner surface 66 of the catheter adapter 14. In some embodiments, the septum 50 is barrel-shaped and has a barrier member 52 on its distal end and a cavity 54 within its a proximal end. When positioned within the channel 60, the barrier member 52 of the septum 50 divides the inner lumen 36 of the catheter adapter 14 into a forward fluid chamber 62 and a rearward fluid chamber 64. Thus, the presence of the septum 50 can limit passage of fluid between the forward and rearward fluid chambers 62 and 64.

In some embodiments, the barrier member 52 of the septum 50 includes a slit 56. The slit 56 can provide selective access or flow of a fluid through the barrier surface 52 as it opens (activates) and closed (deactivates) in response to the septum activator 80. In some embodiments, the slit 56 is configured to remain in a closed, fluid-tight position until activated or opened by advancing a septum activator 80 through the slit 56 in a distal direction 72. In some instances, the barrier member 52 comprises a single slit 56. In other instances, the barrier member 52 is modified to include multiple slits 56, such as two slits 56 forming a cross or x-shape. In other instances, the barrier member 52 is modified to include three slits 56 forming a Y-shape.

The septum activator 80 comprises a probe-like structure serves to activate and deactivate the septum 50 in response to the insertion and removal of the probe member 46. The Septum activator 80 can be primarily housed in the rearward chamber 64 of the catheter adapter 14, proximal the septum 50. In some embodiments, the septum activator 80 is a tubular body 82 having a distal end 84 and a proximal end 86. The tubular body 82 can be made of a rigid or semi-rigid material, such as a plastic or metallic material. The tubular body 82 can have an inner lumen 88 that facilitate flow of a fluid and/or liquid through the septum activator 80 when the septum activator 80 pierces through the slit 56 of the septum 50.

Figure 5:
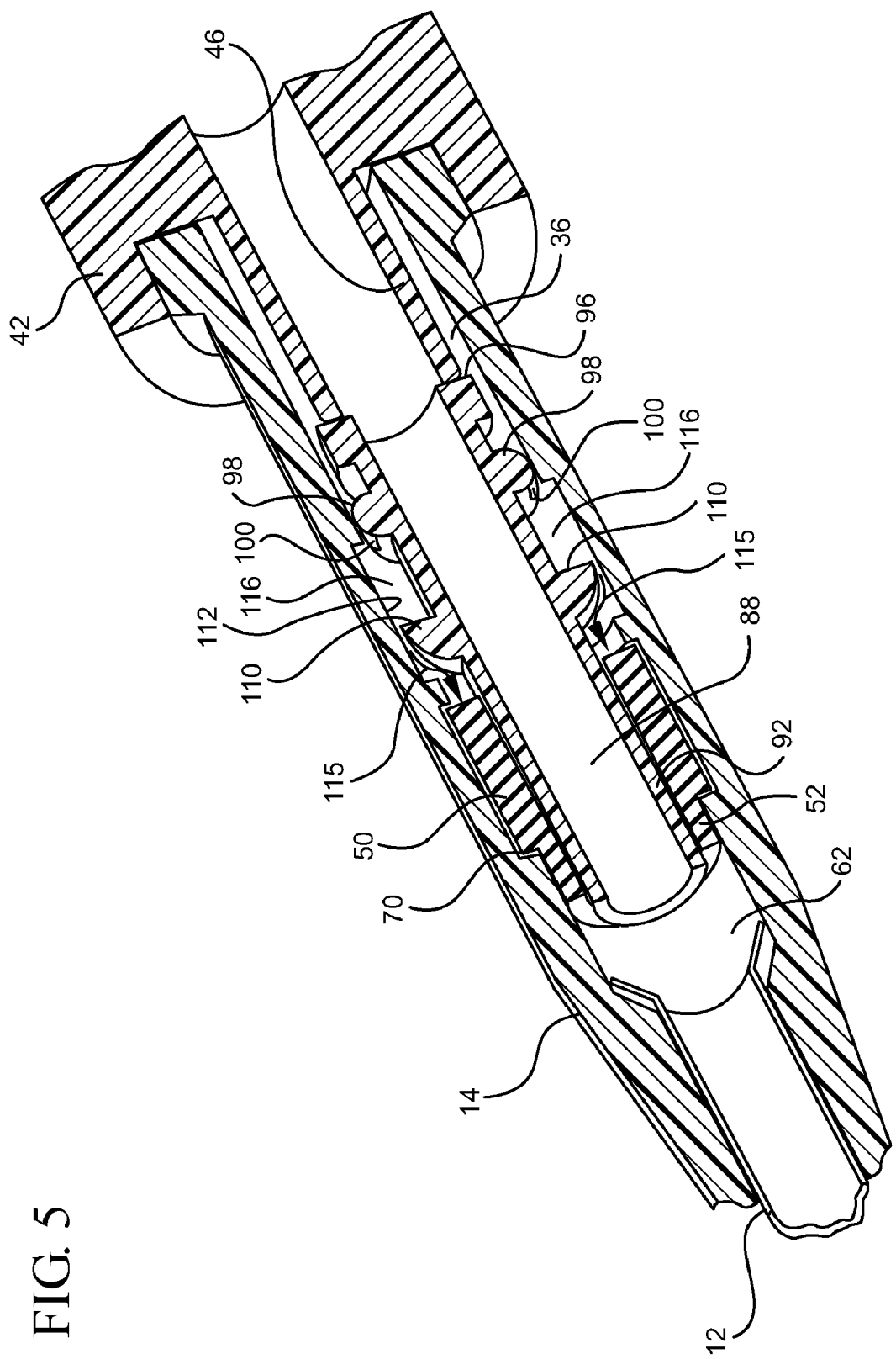
FIG. 5 is a perspective cross-sectioned view of the catheter assembly of FIG. 4 with the septum activator in an activated position, according to some embodiments.

The distal end 84 of the tubular body 82 can be configured to be compatibly inserted into the cavity 54 within the proximal side of the septum 50 so that it is positioned where it can pierce through the slit 56 of the barrier member 52 to form a fluid path therethrough. The distal end 84 further includes a leading surface 90 that can be inserted through the opening 54 of the septum 50 to a position proximal to the barrier member 52 of the septum 50, as shown in FIG. 6. When forced distally, the leading surface 90 advances through the slit 56 as the septum activator 80 is moved between a deactivated position, as shown in FIG. 4, to an activated position, as shown in FIG. 5.

To properly align the septum activator 80 within the inner lumen 36 of the catheter adapter 14, one or more alignment structures can be included between the outer surface of the septum activator 80 and the inner surface 66 of the catheter adapter 14. For example, as shown in FIG. 4, one or more alignment fins 110 can protrude from the outer surface of the septum activator 80 and inserted within one or more alignment groove 112 formed within the inner surface 66 of the catheter adapter 14. As the septum activator translates longitudinally within the catheter adapter, the one or more alignment fins 110 each track within the one or more alignment groove 112 to maintain septum activator 80 properly aligned within the catheter adapter 14. In some configurations there are three, four, five, or six alignment fins 110, each inserted within one of a like number of alignment grooves 112.

In addition to activating the septum 50, the septum activator 80 can form barrier surfaces of a flashback chamber 116 that contains fluid therein. Barrier surfaces define the exterior of the flashback chamber 116 and can prevent fluid from therethrough. Flashback generally occurs when the introducer needle 22 and/or the catheter 12 enter a blood vessel of a patient, piercing the blood vessel, and opening a fluid path through the catheter 12. The patient's blood pressure forces blood out the blood vessel into the catheter assembly 10. When the catheter adapter 14 or a portion thereof is transparent or semi-transparent, as it is in some embodiments, blood flow through its inner lumen 36 is observable and can indicate to a clinician that the catheter 12 is currently located within the blood vessel of the patient. If blood flow stops, the clinician can understand that the catheter 12 is no longer located within the blood vessel or that some other factor is restricting blood flow through the catheter 12. Thus, a flashback that can last long enough for a clinician to properly place a catheter is desirable.

Referring to FIG. 4, in some embodiments, the blood generally enters the catheter assembly 10 and follows a flashback path 114 through the catheter assembly 10. The fluid path 114 enters into the forward chamber 62, which can be a first flashback chamber since it includes the volume that can be observed to be filled with blood. Next, blood flows through flow restrictors 70 disposed around the septum 50 and enters the flashback chamber 116, which can be a second flashback chamber. In instances where the catheter adapter 14 or a portion thereof is transparent or semi-transparent, a clinician can observe this flow of blood filing these chambers, which indicates proper placement of the catheter 12.

As mentioned, during flashback, blood enters the flashback chamber 116 through one or more flow restrictors 70 interposed between the septum 50 and the inner surface 66 of the catheter adapter 14 to provide a flow path for flashback. Generally, the septum 50 sits with a groove or channel 60 that comprises a recessed portion of the inner surface 66 of the catheter adapter 14. The outer diameter of the septum 50 can compatibly and securely sit within the channel 60. For example, in some embodiments the outer diameter of the septum 50 is selected to be both slightly smaller than the diameter of the channel 60 and slightly larger than the diameter of the inner lumen 16. As such, the septum 50 is retained within the channel 60 during use of the catheter assembly 10. The flow restrictors 70 can permit the passage of air and fluid therethrough, while generally regulating the flow rates. The size of the cross-sectional area of each flow restrictor can at least partially control the rate of fluid flowing therethrough. For example, as the cross-sectional area of the flow restrictors 70 increases, the potential rate of fluid flow through the flow restrictors 70 increases. Likewise, flow restrictors 70 having smaller cross sectional areas will decrease the flow of fluid therethrough. The sizes and configurations of flow restrictors 70 and other components are described in detail below.

The volume between the septum activator 80, the catheter adapter 14, and the septum 50 can at least partially define a flashback chamber 116, shown in FIG. 4. In some configurations, the outer surface 92 of the septum activator 80 is a barrier surface of the flashback chamber 116 that prevents fluid from flowing between the inner lumen 88 of the septum activator 80 and the volume of space around the outer surface 92 of the septum activator 80. Accordingly, as shown, in some instances, the septum activator 80 is a solid tube only a single proximal and a single distal opening.

As fluid enters the flashback chamber 116, a seal 98 disposed between the septum 50 and the inner surface 66 of the catheter adapter 14 can prevent the fluid from flowing out the proximal end of the catheter adapter 14. In some embodiments, the seal 98 encircles the septum activator 80, as shown, forming a barrier surface of the flashback chamber 116 that prevent the proximal flow of fluids past the seal 98. In some embodiments, the seal 98 is coupled to the outer surface 92 of the septum activator 80. In other embodiments, the seal 98 is coupled to the inner surface 66 of the catheter adapter 14. By adjusting the location of the seal 98, the volume of the flashback chamber 116 increases or decreases. Thus, the seal 98 can be positioned at various locations between the proximal and distal ends of the septum activator 80. For instance, the seal 98 can be disposed on a proximal portion of the septum activator 80, such as the proximal half of the septum activator 80, as shown. More specifically, in a non-limiting example, the seal 98 is disposed on the proximal end 86 of the septum activator 80, as shown in FIG. 8, which is described below. Further, the seal 98 can circumscribe a portion of the outer surface 92 of the septum activator 80 in a ring-like fashion, as shown, to seal the area around a portion of the septum activator 80.

In some embodiments, the seal 98 can provide a fluid-tight barrier about the septum activator 80 that prevents blood from leaking through the proximal end of the flashback chamber 116 and out the catheter assembly 10. For instance, the seal 98 can have an outer diameter greater than or equal to the inner diameter of the lumen 36 of the catheter adapter 14 to block fluid flow through the entire area between the septum activator 80 and the catheter adapter 14. The seal 98 can also be made of a flexible material so that it can adequately conform to the inner surface 66 of the catheter adapter 13 to form a seal thereon. Accordingly, the seal 98 can comprise a non-rigid material, such as an elastomeric material. In other instances, the seal 98 is made of other flexible, semi-flexible, or semi-rigid materials that can provide a fluid-tight seal between the catheter adapter 14 and the septum activator 80.

Initially during flashback, blood flowing into the catheter 12 forces air to flow through the flow restrictors 70. This initial infusion of blood can be very quick as blood rushes through the catheter 12 into the forward chamber 62. The forward chamber 62 can serve as a first flashback chamber that provides a first indication to clinicians that blood is flowing into the catheter assembly 10. By observing this flow of blood, a clinician can verify that the catheter 12 has entered a blood vessel. However, in some instances, the time in which this initial flashback occurs is very quick and not be long enough for a clinician to verify proper catheter placement. Accordingly, in some configurations, a second flashback chamber 116 is provided on the proximal side of the septum 50 that provides extended flashback indications. Accordingly, air and blood from within the forward chamber 62 can flow through the flow restrictors 70 disposed between the septum 50 and the catheter adapter 14 into the second flash chamber 116. Because the size of the flow restrictors 70 controls the flow of blood therethrough, the rate of flashback into the second flashback chamber 116 can be regulated to provide a longer average flashback periods.

When blood begins to flow into the catheter assembly, a positive pressure develops within the forward chamber 62, the first flashback chamber, and the second flashback chamber 116. This pressure can reduce or prevent the flow of blood into the catheter assembly 10, thus preventing a desired flashback of the patient's blood into the catheter adapter 14. Thus, some embodiments include features or elements to enable airflow through or around the seal 98, to relieve this positive pressure by permitting air, but not blood, to exit therethrough. As such, some embodiments of the present invention provide a complete observable flashback, as generally desired for infusion procedures.

In some embodiments, the seal 98 of the septum activator 98 is modified to include one or more flow restrictors 100. In other embodiments, one or more vents 120 (shown in FIG. 6), in the form of channels, are interposed between the seal 98 and the inner surface 66 of the catheter adapter 14. These vents 100 relieve the positive pressure within the flashback chambers 62, 116 by providing an access for air to bypass the seal 98 into the exterior environment. In some embodiments, the vents 100 are constructed by removing portions of the seal 98 surface, resulting in a plurality of generally parallel grooves. In other embodiments, the vents 100 are formed as channels through the seal 98 rather than on the surface of the seal 98.

In some embodiments, the rate at which air and/or fluid flows through the vents 100 in the seal 98 is adjusted by manufacturing the catheter adapter 14 to include a greater or lesser number of vents 100 or by changing the cross-sectioned area of the vents 100. Thus, in some embodiments the rate at which air and/or fluid flows out of the second flashback channel 116 is increased by manufacturing a catheter adapter 14 to have either an increased number of vent 100, or vents 100 a greater cross-sectioned area. Conversely, in other embodiments the rate at which air and/or fluid flows from the second flashback chamber 116 is decreased by manufacturing a catheter adapter 14 with either a decreased number of vents 100, or vents 100 having a lesser cross-sectioned area.

One having skill in the art will appreciate that the blood pressure of the patient is largely responsible for the rate at which blood and air flows through the septum 50 and the vents 100 in or around the seal 98. As such, the flow rate through the system is affected by the combined effective hydraulic diameter of all flow paths. Thus, in some embodiments, the hydraulic diameter of the vents 100 is modified to increase or decrease the rate of flow through the catheter assembly 10. In other embodiments, the hydraulic diameter of the vents 100 are decreased thereby resulting in substantially reduced or stopped flow through the ventilation means. The governing equation for controlling the flow rate through the ventilation means is given in Equation 1, where BP is the blood pressure, A is the surface area of the ventilation means, ó is the surface tension of the blood, and P is the perimeter of the ventilation means.

$$BP(A) = ó(P) \qquad \text{Equation 1}$$

Thus, according to Equation 1, when the perimeter of a vent is small, the vents 100 will allow air venting, but will prevent blood flow due to the relatively high surface tension (ó) of blood. However, when the perimeter of the vent is increased, the surface tension between the blood and the vent 100 is decreased thereby enabling the blood to slowly leak through the vents and around the septum to provide desirable, yet controlled flashback. Therefore, by adjusting the variable of Equation 1, a desired flow will be achieved. Thus, based on the size and/or number of vents around the septum, the catheter assembly design will provide customized, controlled, and predictable blood flow through the seal 100.

In some embodiments, the one or more vents 100 are designed to allow the flow of air and stop the flow of blood. In some embodiments, the number of vents 100 is between 1 and 40. In other embodiments, the number of vents 100 is between 1 and 20. In some embodiments, six or more vents 100 are included. While in other embodiments, five or fewer vents 100 are included. Accordingly, in some embodiments, the vents 100 have a cross sectional area between about 0.000007 to 0.00004 inches$^2$. In other embodiments, the vents 100 have a cross sectional area between about 0.00001 to 0.00003 inches$^2$. In other embodiments, the vents 100 have a cross sectional area of about 0.00002 inches$^2$. For instance, in some embodiments, the vents 100 have a height of about 0.001 to 0.003 inches and a width of about 0.010 inches. In other embodiments, the vents have a height of about 0.002 to 0.003 inches and a width of about 0.005 inches.

Similarly, the one or more flow restrictors 70 between the septum 50 and the inner surface 66 of the catheter adapter 14 can be specifically configured to permit blood and air to pass therethrough at an estimated range of flow rates. For instance, the one or more flow restrictors 70 can permit blood to flow therethrough at a rate between about 10 to 200 ml/hr. In other instances, the one or more flow restrictors 70 can permit blood to flow therethrough at a rate between about 15 to 150 ml/hr. In yet other instances, the one or more flow restrictors 70 can permit blood to flow therethrough at a rate between about 50 to 100 ml/hr. At these rates, the rate of blood flow into the flashback chamber 116 can be paced to provide a clinician with adequate time to correctly locate the catheter within a patient's blood vessel. Accordingly, in some embodiments, the flow restrictors 70 have a cross sectional area greater than 0.00003 inches$^2$. In other embodiments, the flow restrictors 70 have a cross sectional area greater than 0.00004 inches$^2$. In other embodiments, the vents 100 have a cross sectional area of about 0.0001 inches$^2$. In other embodiments, the vents 100 have a cross sectional area of about 0.001 inches$^2$.

Referring now to FIG. 5 a cross-sectional view of the catheter assembly 10 is shown following activation of the septum 50 via the septum activator 80. Upon insertion of the coupler 42 into the proximal opening 26 of the catheter adapter 14, the probe member 46 of the coupler 42 contacts the contact surface 96 of the septum activator 80. The septum activator 80 is advanced in a distal direction 72 as the coupler 42 is further inserted into the lumen 36 of the catheter adapter 14. As the coupler 42 is advanced farther into the lumen 36, the probing surface 92 of the septum activator 80 passes through the barrier member 52 of septum 50. As such, the probing surface 92 of the septum activator 80 is positioned within the forward chamber 62 providing a fluid pathway through the opened slit 56 of the septum 50.

During septum activation, the volume of the flashback chamber 116 decreases as the septum activator 80 advances in the distal direction 72. The decrease in volume can create a positive pressure within the flashback chamber 116 that can cause fluids within the flashback chamber 116 to flow back through the flow restrictors 70 into the forward chamber 62, along the fluid flow path 115. This fluid can then be flushed out the catheter assembly 10 with the infusion of fluids from the intravenous tubing 40.

In some embodiments, the catheter assembly 10 is configured to permit the septum activator 80 to return to a deactivated position entirely within the rearward chamber 64 following removal of the coupler 42 from the catheter adapter 14. Thus, when the coupler 46 is removed or detached from the catheter assembly 10, the fluid pathway through the septum 50 is reclosed.

Reference will now be made to FIG. 6, a septum 104 is depicted, according to some embodiments. As shown, an outer surface 108 of the septum 104 is modified to include a plurality of recessed grooves 106. The recessed grooves 106 provide pathways between the forward and rearward chambers 62 and 64 through which air and/or fluid may flow. Thus, in some embodiments, the channel 60 does not include air flow restrictor channels 70, but rather the outer surface 108 of the septum 104 is modified to provide desired flow between the forward and rearward chambers 62 and 64. The shape and size of these grooves can be selected, as mentioned, to provide the desired flow rate therethrough. For instance, the one or more vents 132 can permit blood to flow therethrough at a rate between about 10 to 200 ml/hr. In other instance, the one or more vents 132 can permit blood to flow therethrough at a rate between about 15 to 150 ml/hr. In yet other instances, the one or more vents 132 can permit blood to flow therethrough at a rate between about 50 to 100 ml/hr.

Reference will now be made to FIGS. 7 to 14, which depict alternative embodiments of septum activators that provide selective opening therein for flushing out the flashback chamber 116. The septum activators can include an inner tubular body 115 and an outer 113 tubular body, which can be moved in relation to each other between a first and a second position. Herein reference is made to the movement of either the inner tubular body or the outer tubular body. These references are merely representational. It will be understood that in other embodiments, either or both of the tubular bodies can be moved to change the relative positions of the inner and outer tubular bodies in relation to each other.

In some configurations, in a first position, a plurality of openings on each of the inner 115 and outer 113 tubular bodies do not overlap, and no fluid can pass between the inner lumen 88 of the inner tubular body 115 and the flashback chamber 116. The septum activator can be in this first position during flashback so that fluid entering the flashback chamber 116 remains therein. In some configurations, in a second position, the plurality of openings on each of the inner 115 and outer 113 tubular bodies overlap, and fluid can pass between the inner lumen 88 of the inner tubular body 115 and the flashback chamber 116. The septum activator can be in this second position following flashback during fluid infusion through the catheter assembly 10 so that fluid in the flashback chamber 116 can be flushed.

Figure 7:
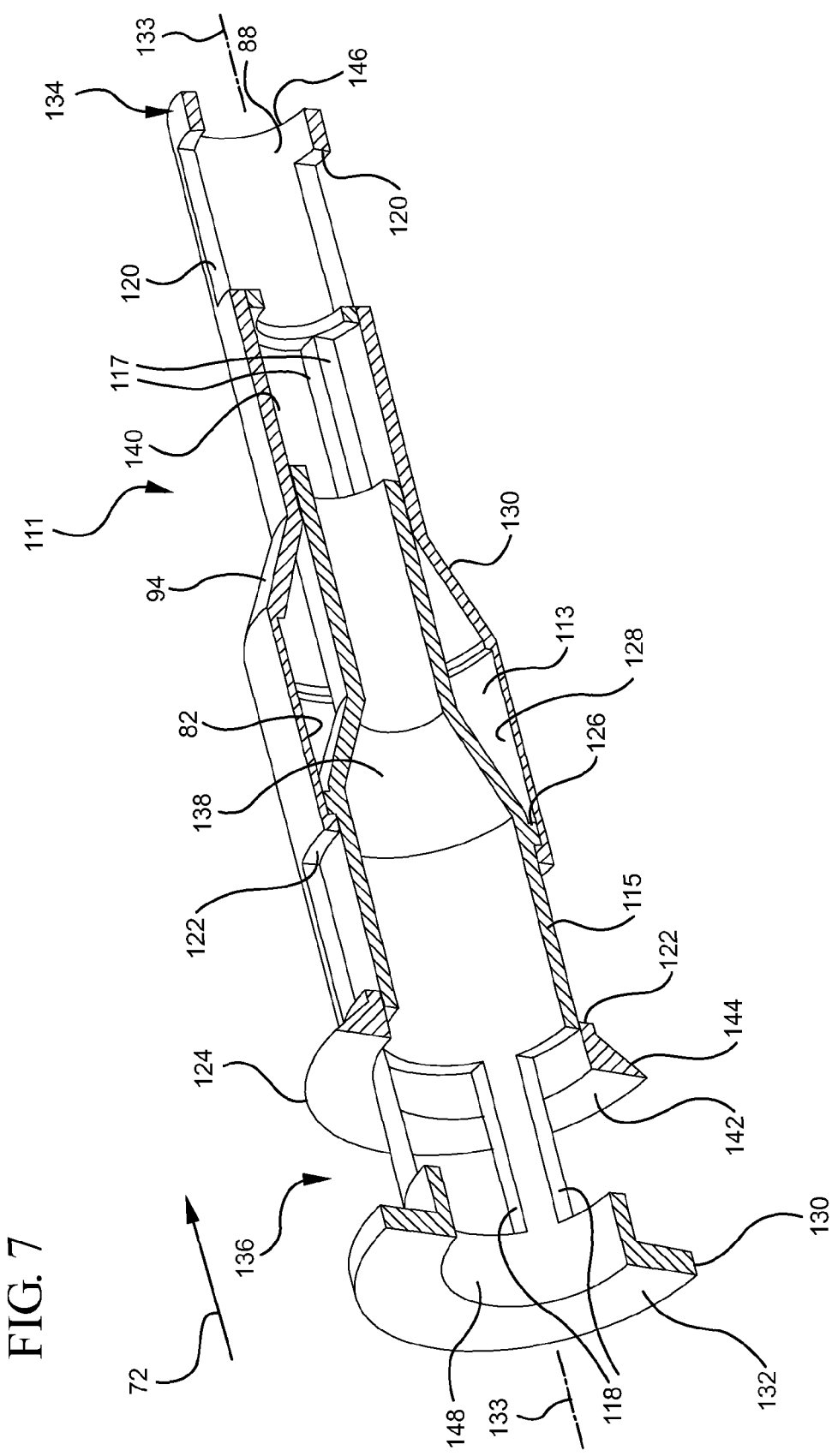
FIG. 7 is a perspective cross-sectioned view of a septum activator in a first position, according to some embodiments.
Figure 9:
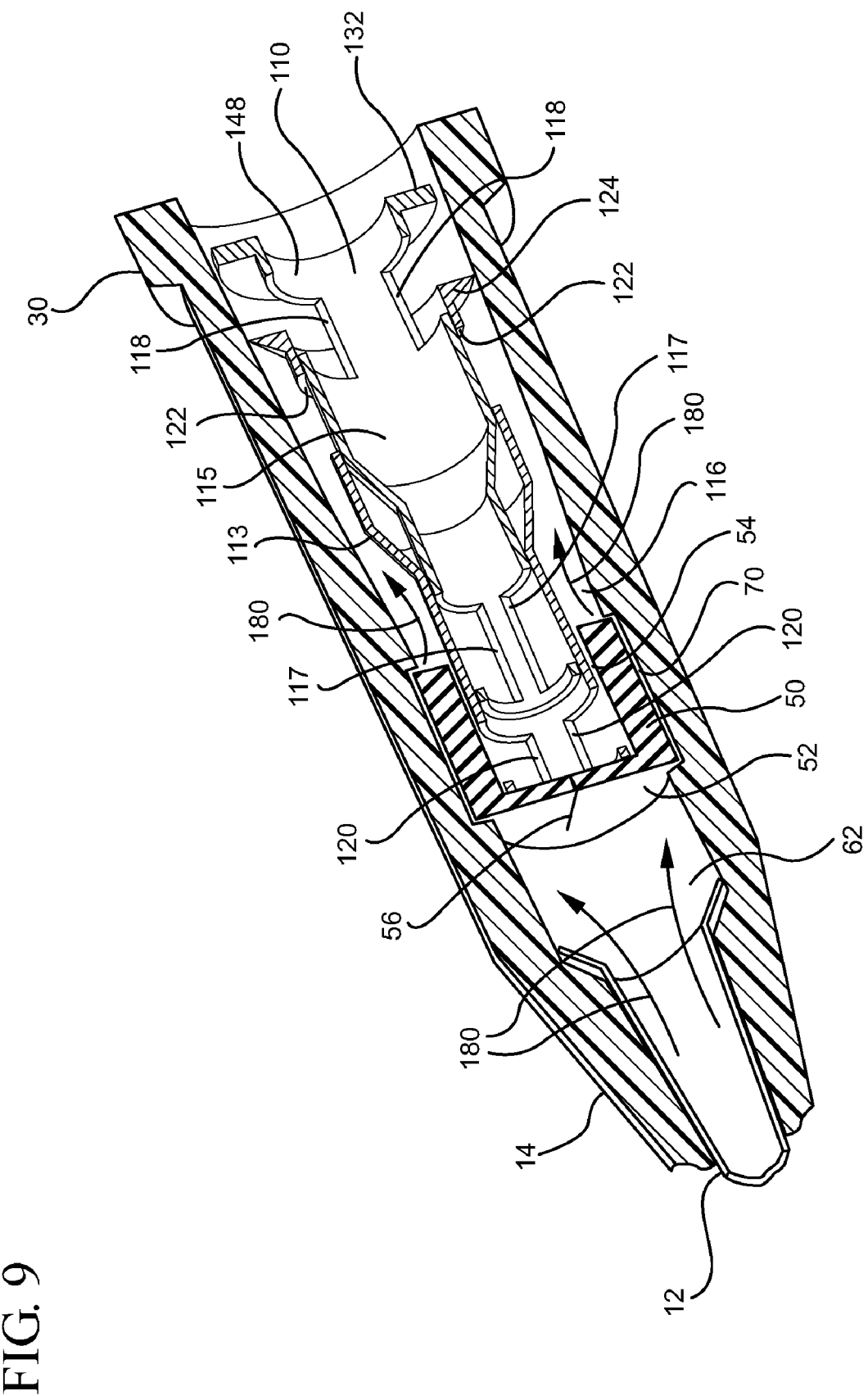
FIG. 9 is a perspective cross-sectioned view of a catheter assembly with a septum activator in a deactivated position in relation to the septum, according to some embodiments.

Referring to FIGS. 7-10, a septum activator 111 is depicted having an outer tubular body 113 that has openings 122 in its proximal portion 136 and openings 120 in its distal portion 134. An inner tubular body 115 is located within inner lumen 140 of the outer tubular body 113. The inner tubular body 115 also has openings 118 in its proximal portion and openings 117 in its distal portion. As depicted in FIG. 7, the inner tubular body 115 is in a first position relative to the outer tubular body 113. In this position, the openings of the inner 115 and outer 113 tubular bodies do not overlap. In this first position, as shown in FIG. 9, the portions of the septum activator 111 that form barrier surfaces to the flashback chamber 116 are closed, such that fluid cannot pass between the inner lumen 88 of the inner tubular body 115 and the flashback chamber 116. As further shown, in this position, the distal-most opening 120 of the outer tubular body 113 is open, but is separated from the flashback chamber 116 since it is inserted within the cavity 54 of the septum 50, as shown in FIG. 9. The proximal-most opening 118 of the inner tubular body 115 is also open, but it is disposed proximal the seal 124, thus not forming a barrier surface of the flashback chamber 116. Thus, in some embodiments, each opening between the septum 50 and the seal 124 is closed when the inner 115 and outer 113 tubular members are in a first position.

Figure 10:
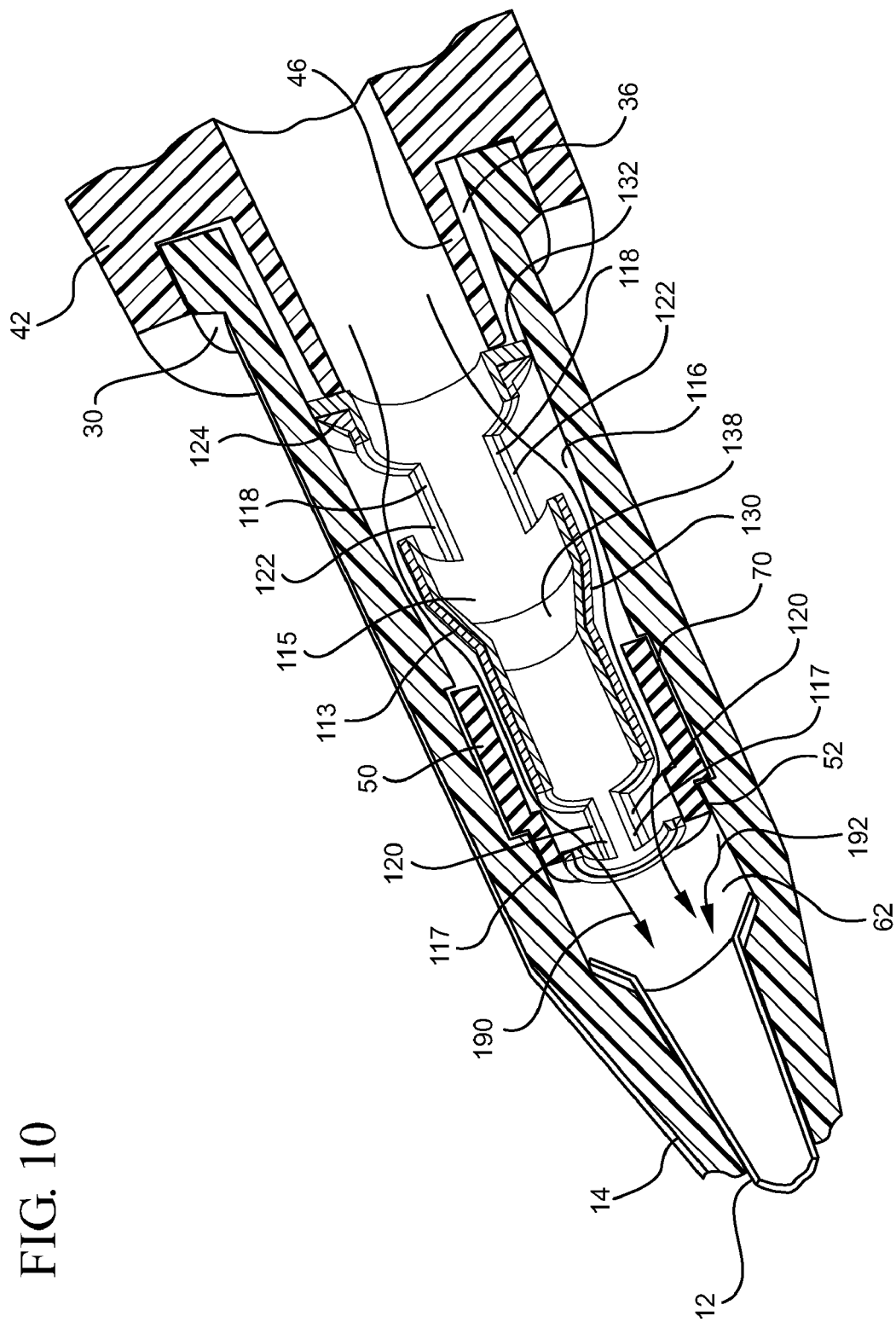
FIG. 10 is a perspective cross-sectioned view of the catheter assembly of FIG. 9 with the septum activator in an activated position in relation to the septum, according to some embodiments.

As depicted in FIG. 8, the inner tubular body 115 is in a second position relative to the outer tubular body 113. In this position, the openings of the inner 115 and outer 113 tubular bodies overlap forming openings that extend through both the inner 115 and the outer 113 tubular bodies. In this second position, as shown in FIG. 10, the overlapping openings of the septum activator 111 create openings in the barrier surfaces of the flashback chamber 116 that allow fluid to pass between the inner lumen 88 of the inner tubular body 115 and the flashback chamber 116. In some instances, as the openings overlap, the flashback chamber 116 is filled with blood or other fluids. Thus, fluid can be forced out the flow restrictors 70 or it can enter the inner lumen 88 of the inner tubular body 115 as fluid is infusing into the catheter adapter 14. Accordingly, the overlapping openings drain and/or flush fluid from the flashback chamber 116.

To provide a fluid tight barrier that prevents the escape of fluids from the flashback chamber 116 into the inner lumen 88 of the inner tubular body 115, the outer surface of the inner tubular body 115 can have approximately the same dimensions and geometry as the inner surface of the outer tubular body 113. Furthermore, in some embodiments, a lubricant, such as a non-wetting lubricant can be disposed between the inner tubular body 115 and the outer tubular body 113 that assists to reduce or limit fluid flow therethrough.

In some embodiments, the septum activator 111 includes a seal 124 that forms a barrier surface of the flashback chamber 116. The seal 124 can function similarly to the seals 98 of FIGS. 3-5. As shown, the seal 124 can have a triangular shape, with an angled distal surface 144 and a flat proximal surface 142 that faces proximally. The seal 124 can have an outer diameter that is equal to or slightly larger than the inner diameter of an inner lumen 36 of a catheter adapter 14 so that the seal forms a fluid-tight seal about the septum activator 111. Also, similar to the seals 124 illustrated in FIGS. 3-5, the seal 124 can include one or more vents (not shown) shaped and sized to permit the passage of air, but not blood therethrough. The vents can be disposed on the outer surface of the seal 124 or through the seal 124.

To enable the overlap of two or more openings, in some configurations, the inner tubular body 115 and the outer tubular body 113 have a corresponding array of openings. For instance, each of the openings 117, 118 of the inner tubular body 115 can align with an opening 120, 122 of the outer tubular body 113 when in the second position. In non-limiting examples, the inner tubular body 115 and the outer tubular body 113 each have between one and fifteen openings that align with a like number of openings in the outer tubular body. For example, the inner tubular body 115 can have six openings 117, 118 that overlap with six openings 120, 122 of outer tubular body 113 when in the second position, as shown. In another example, the inner tubular body 115 and the outer tubular body 113 each have eight openings. In other configurations, the openings of the inner tubular body 115 do not simultaneously align with those of the outer tubular body 113, but each opening can align with another at varying points along the movement between the first and the second positions to provide a large opening surface area at multiple locations between the first and second positions.

In some configurations, such as those depicted in FIGS. 7-10, the inner tubular body 115 moves from a first position to a second position relative to the outer tubular body 113 as the inner tubular body is translated along the longitudinal axis 133 of the septum activator 111. For instance, in some configurations, one or both of the inner 115 or the outer 113 tubular body is translated distally along the longitudinal axis 133. In some configurations, one or both of the inner 115 or the outer 113 tubular body is translated proximally along the longitudinal axis 133. As depicted in FIG. 8, the inner tubular body 115 moves from a first position to a second position relative to the outer tubular body 113 as the inner tubular body 115 is translated distally along the longitudinal axis 133. In some embodiments, the force required to translate the inner tubular body 115 within the outer tubular body 113 is less than the fore required to pieced the septum 50, so that the septum activator 80 begins to pierce the septum 50 only after the inner tubular body 115 is in the second position relative to the outer tubular body 113. In other embodiments, the forces are equal, or the force required to pierce the septum 50 is less than the translation force.

To prevent removal of the inner tubular body 115 from the outer tubular body 113, the septum activator 111 can include one or more interlocking features between these two bodies. As shown in FIGS. 7-8, in some embodiments, a recess 128 is formed on the inner surface of the outer tubular body 115 that receives an annular ring 126 that is formed on the outer surface of the inner tubular body 115. The recess 128 can extend longitudinally far enough to permit the inner tubular body 115 to translate between the first and second positions. Additionally, the recess 128 can limit the movement of the inner tubular body 115 so that it cannot be removed from the outer tubular body 113 or be inserted too far distally within the outer tubular body 113.

In some embodiments, tapered portions 130, 138 of the outer 113 and inner 115 tubular bodies, rather than one or more interlocking features, limit the distal movement of the inner tubular body 115 within the outer tubular body 113. For example, as shown, as the inner tubular body 115 is translated distally, its tapered portion 138 contacts the tapered portion 130 of the outer tubular body 113 which restricts any further distal movement of the inner tubular body 115.

In some configurations, the inner tubular body 115 and the outer tubular body 113 have substantially the same lengths. By having similarly lengths, the inner tubular body 115 and the outer tubular body 113 form a septum activator 111 of constant wall thickness when in the second position, as shown in FIG. 8. However, as shown in FIG. 7, in a first position, the inner tubular body 115 can be staggered from the outer tubular body 113, forming a longer septum activator 111.

FIGS. 9-10 depict a septum activator 111 of FIG. 8-9 within a catheter assembly 10. Similar to the septum activators 80 of FIGS. 3-5, the septum activator 111 can be configured to be compatibly inserted into the cavity 54 within the proximal side of the septum 50 so that it is positioned where it can pierce through the slit 56 of the barrier member 52 to form a fluid path therethrough. The distal end 134 includes a leading surface that can be inserted through the septum 50 to a position proximal to the barrier member 52 of the septum 50, as shown in FIG. 10.

As shown in FIG. 9, when the septum activator 111 is disposed in a deactivated position in the catheter adapter 12, and the inner tubular body 115 is in a first position relative to the outer tubular body 113, the septum activator 111 forms a barrier surface of the flashback chamber 116. Thus, during flashback, fluid flow along fluid flow path 180 into the flashback chamber 116. When the tubular body 115 is in a first position relative to the outer tubular body 113, the septum activator 111 can form a fluid-tight barrier that prevents fluids from the flashback chamber 116 from entering the inner lumen 88 of the inner tubular body 115. As mentioned, as fluid enters the flashback chamber 116, it can provide a clinician with an observable indicator that the catheter 12 is properly placed.

Referring to FIG. 10, once the catheter 12 is properly placed, a conduit coupler 42 can connect an intravenous tubing 40 to the catheter adapter 14 to begin infusing fluid into the patient. As the conduit coupler is inserted onto the catheter adapter 14, the probe member 46 enters into the inner lumen 36 of the catheter adapter and contacts the contact surface 132 of the inner tubular body 115. As the probe member 46 advances farther distally, it moves the inner tubular body 115 from a first position to a second position, wherein openings 117, 118 in the inner tubular body 115 overlap openings 120, 122 in the outer tubular body 113 forming openings the pass through the septum activator 111. As this point, one or more fluid paths 190 are opened between the inner lumen 88 of the inner tubular body 115 and the flashback chamber 116. When the probe member 46 is completely advanced, the septum activator 111 pierces the septum 50, opening a fluid path therethrough. As fluid is infused into the catheter assembly 10, fluid flows along one or more fluid flow paths 190, 192 in and out of the overlapping openings of the septum activator 111, through the inner lumen 888 of the inner tubular body 115, and/or through the flow restrictors 70 between the septum 50 and the catheter adapter 14. In this manner, fluids within the flashback chamber 116 can be flushed out of the catheter assembly 10.

Figure 11A:
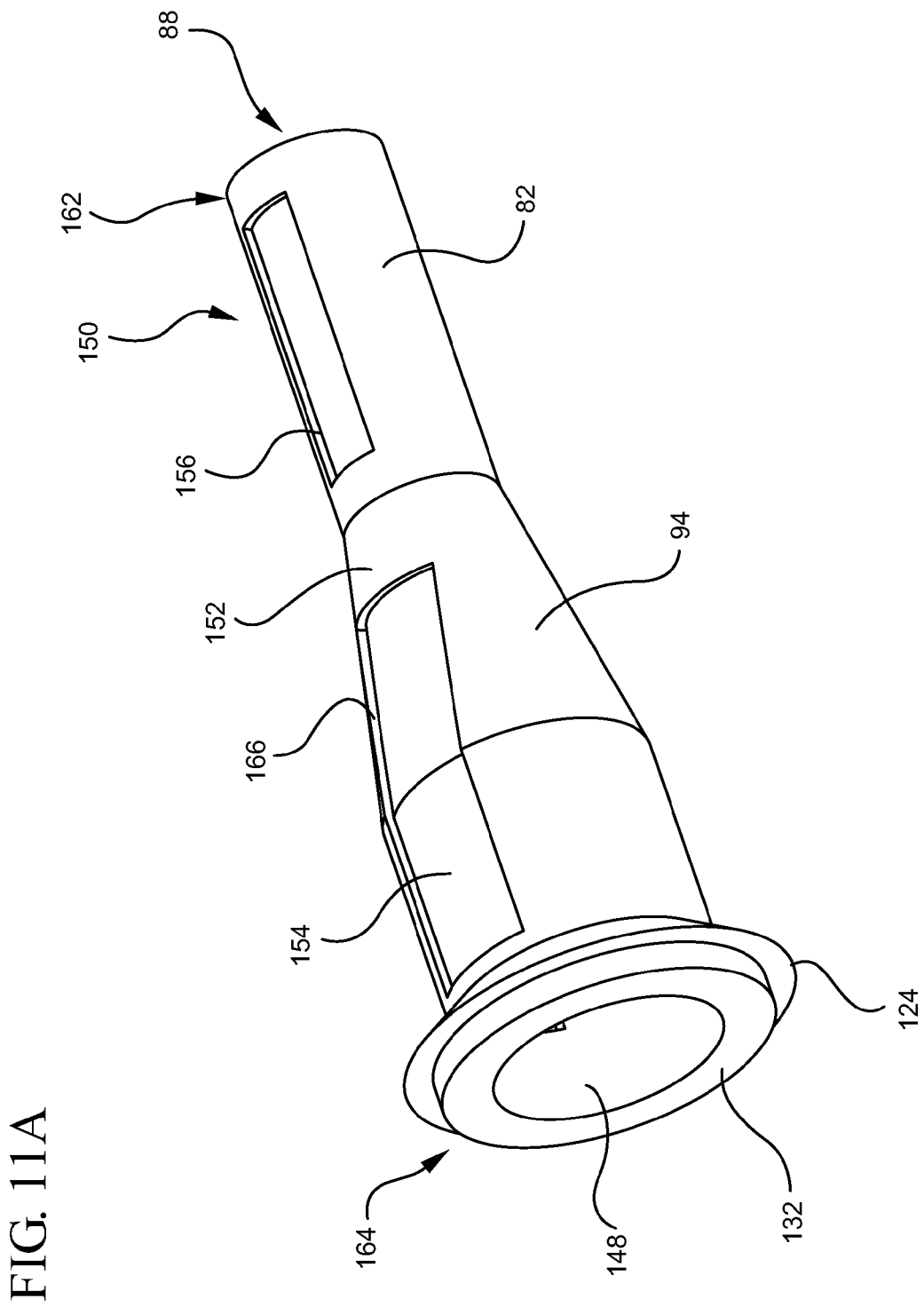
FIG. 11A is a perspective view of another septum activator in a first position, according to some embodiments.
Figure 12A:
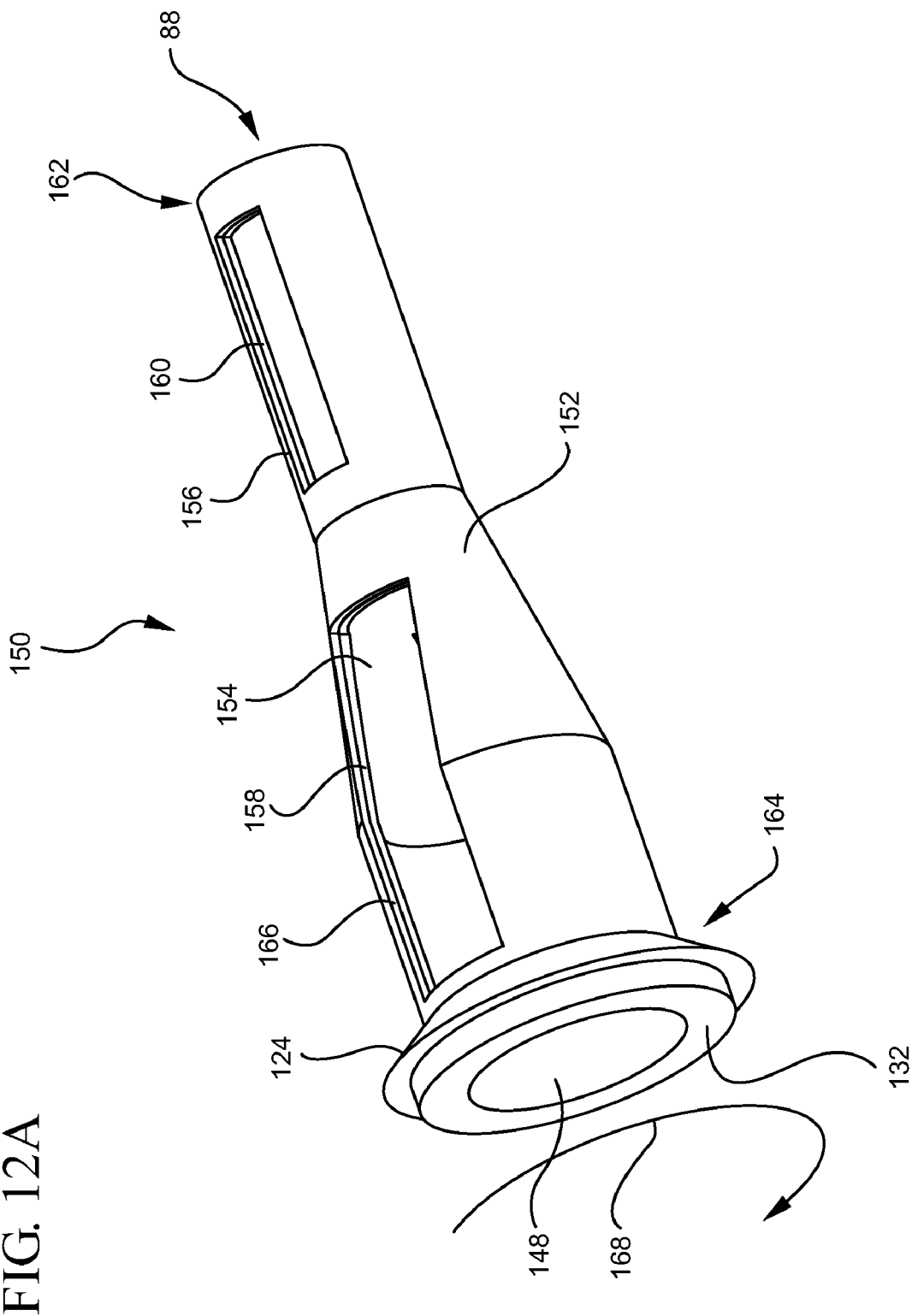
FIG. 12A is a perspective view of the septum activator of FIGS. 11A-11B in a second position, according to some embodiments.
Figure 12B:
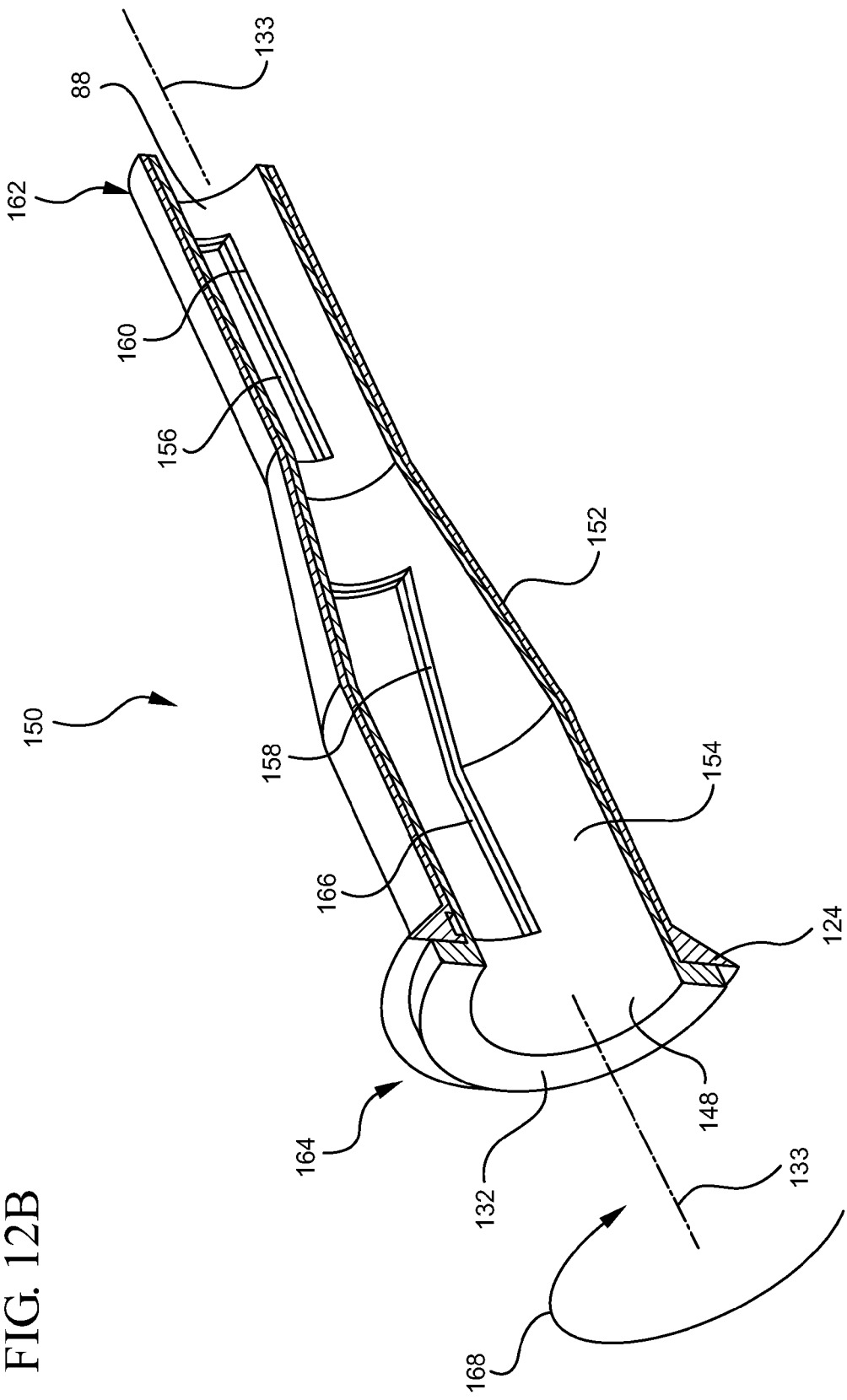
FIG. 12B is a perspective view cross-sectioned of the septum activator of FIG. 12A.
Figure 13:
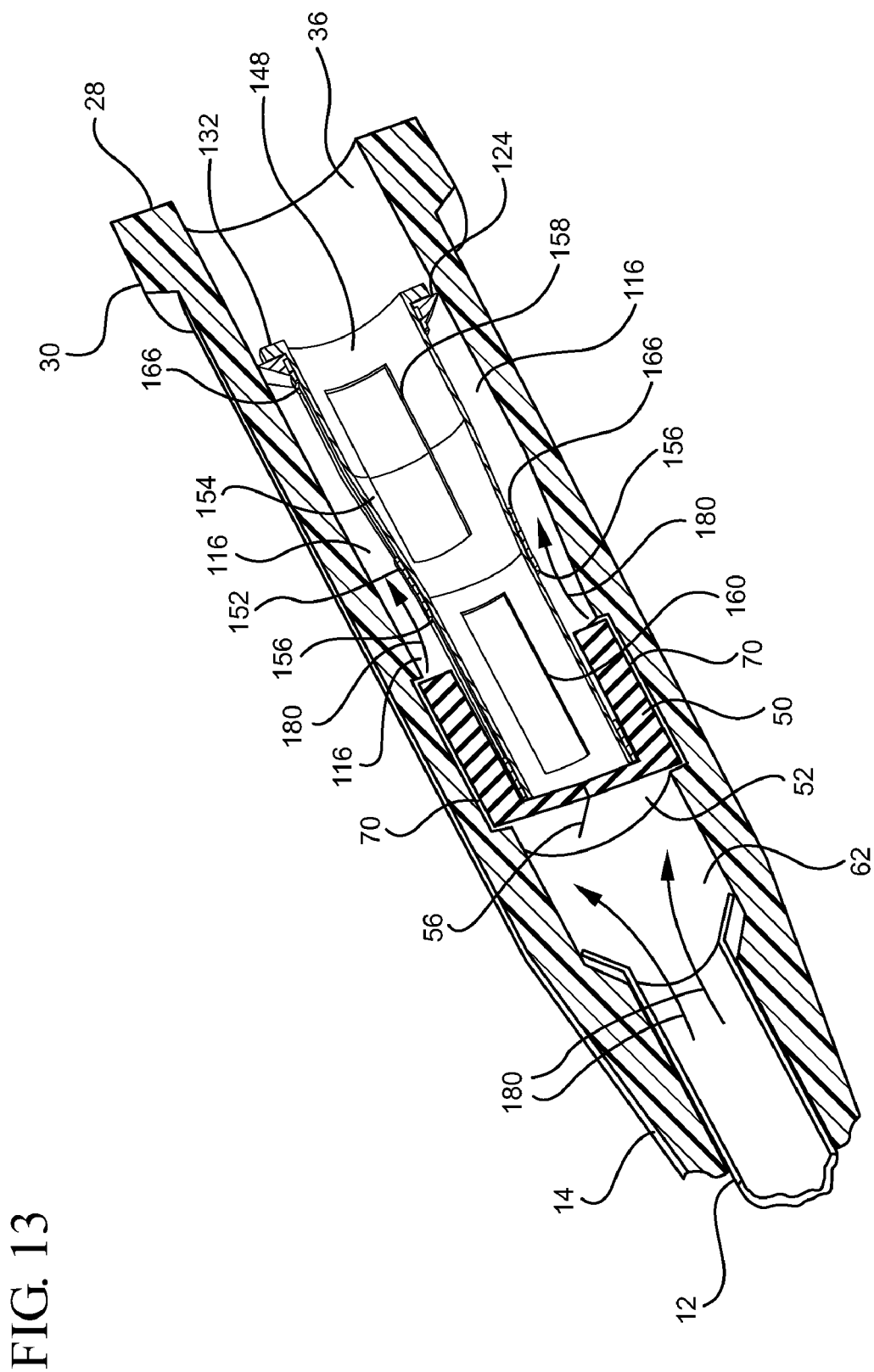
FIG. 13 is a perspective cross-sectioned view of another catheter assembly with a septum activator in a deactivated position in relation to the septum, according to some embodiments.

FIGS. 11A-14 depict alternative embodiments of a septum activator 150 that, like the septum activators of FIGS. 7-10, provides a barrier surface for a flashback chamber 116 that can be selectively opened to flush fluids from the flashback chamber 116. Referring to FIGS. 11A-11B, a septum activator 150 is depicted having an outer tubular body 152 that has openings 166 in its proximal portion 164 and openings 156 in its distal portion 162. An inner tubular body 154 is located within the inner lumen 140 of the outer tubular body 152. The inner tubular body 154 also has openings 158 in its proximal portion and openings 160 in its distal portion. As depicted in FIGS. 11A-11B, the inner tubular body 154 is in a first position relative to the outer tubular body 152. In this position, the openings of the inner 154 and outer 152 tubular bodies do not overlap. In this first position, as shown in FIG. 13, the portions of the septum activator 150 that form barrier surfaces to the flashback chamber 116 are closed, such that fluid cannot pass between the inner lumen 88 of the inner tubular body 154 and the flashback chamber 116.

Figure 14:
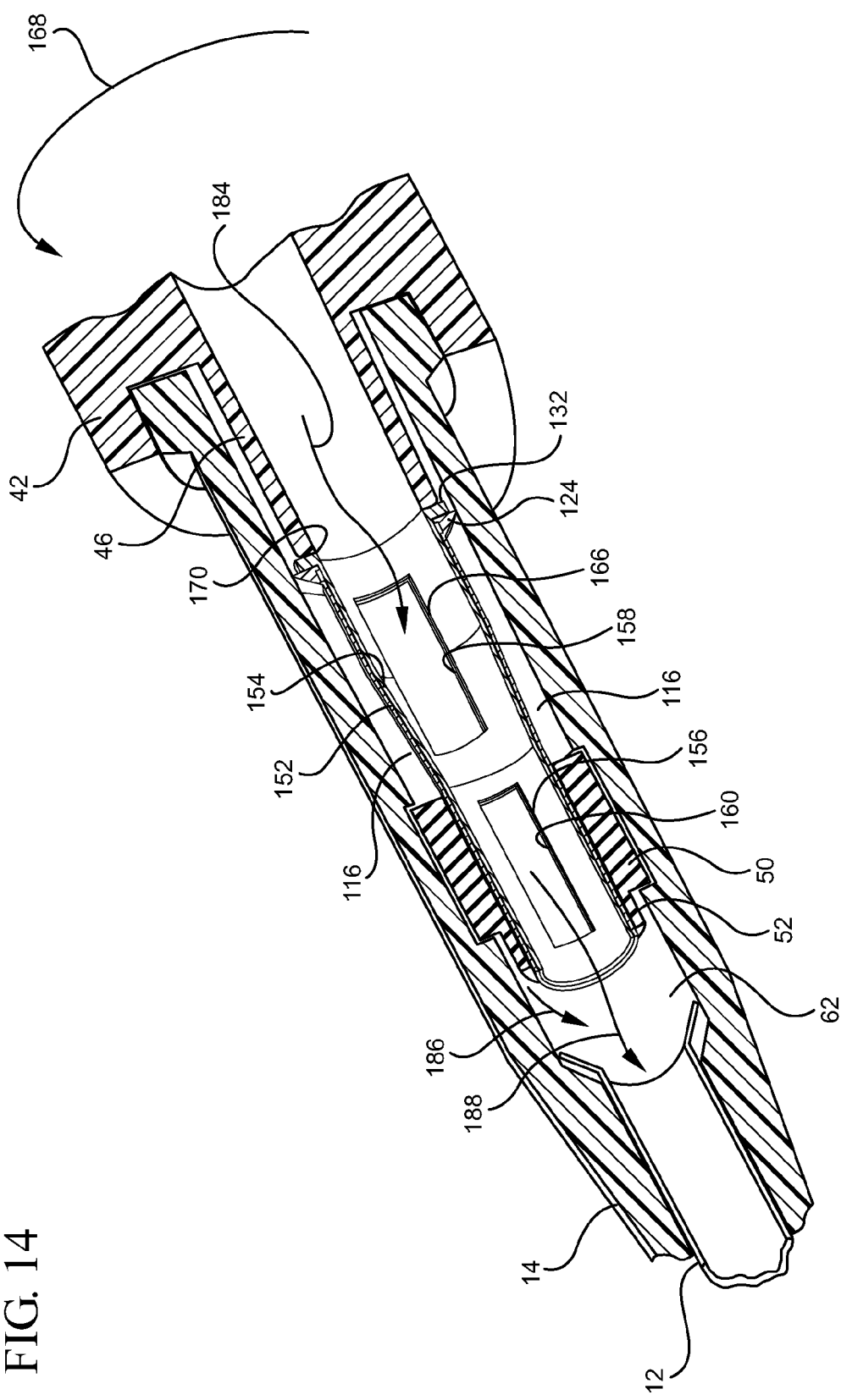
FIG. 14 is a perspective cross-sectioned view of the catheter assembly of FIG. 13 with the septum activator in an activated position in relation to the septum, according to some embodiments.

As depicted in FIGS. 12A-12B, the inner tubular body 154 is in a second position relative to the outer tubular body 152. In this position, the openings of the inner 154 and outer 152 tubular bodies overlap forming openings that extend through both the inner 154 and the outer 152 tubular bodies. In this second position, as shown in FIG. 14, the overlapping openings of the septum activator 150 create openings in the barrier surfaces to the flashback chamber 116 that allow fluid to pass between the inner lumen 88 of the inner tubular body 154 and the flashback chamber 116. Fluid passing from within the inner lumen 88 of the inner tubular body 154 through these overlapping openings enters the flashback chamber 116, thus flushing fluid from the flashback chamber 116.

Aside from having different configurations that enables movement between a first and a second position, the septum activator 150 of FIGS. 11A-14 can have similar features, functions, and properties to those of the septum activator 111 of FIGS. 7-10. For example, in some configurations, the septum activator 150 provides a fluid tight barrier that prevents the escape of fluids from the flashback chamber 116 into the inner lumen 88 of the inner tubular body 154. In some configurations, the septum activator 150 includes a seal 124 that can have one or more vents therein. In some configurations, the inner tubular body 154 of the septum activator 150 has a plurality of openings 158, 160 that align with a like number of openings 166, 156 in the outer tubular body 152. In some configurations, the inner tubular body 154 and the outer tubular body 152 have substantially the same lengths.

As depicted in FIGS. 11A-12B, the inner tubular body 154 moves from a first position to a second position relative to the outer tubular body 152 as the inner tubular body is rotated about the longitudinal axis 133 of the septum activator 150. The rotational direction is illustrated with an arrow 168. In other instances, the direction of rotation is in the opposite rotational direction. As depicted in FIGS. 11A-11B, as the inner tubular body 154 moves from a first position to a second position relative to the outer tubular body 152 openings 158, 160 in the inner tubular body 154 overlap openings 166, 156 in the outer tubular body 152.

Figure 11B:
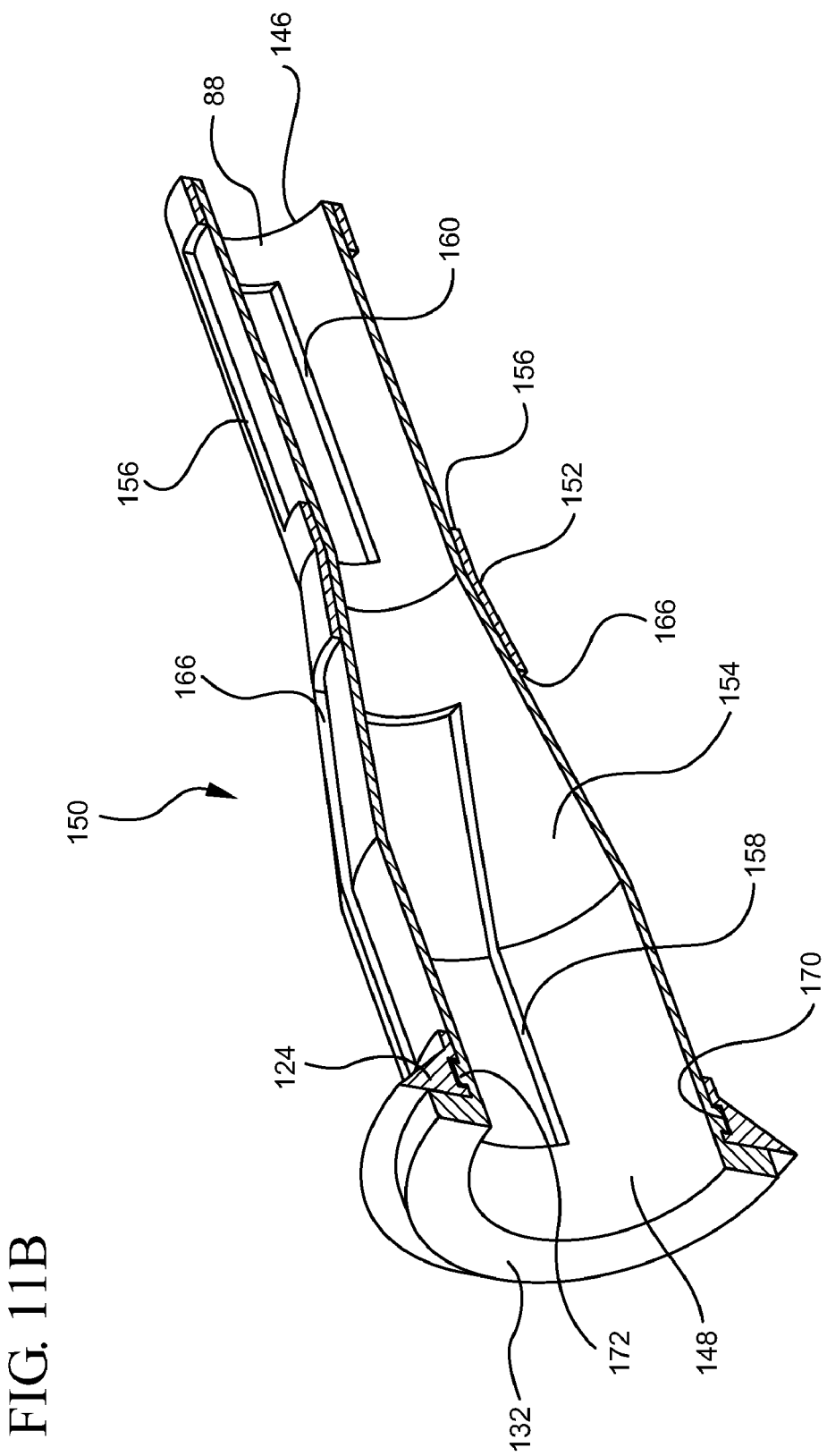
FIG. 11B is a perspective view cross-sectioned of the septum activator of FIG. 11A.

To prevent removal of the inner tubular body 154 from the outer tubular body 152, the septum activator 150 can include one or more interlocking features between these two bodies. As shown in FIGS. 11A-11B, in some embodiments, a groove 170 is formed on the inner surface of the outer tubular body 152 that receives an annular ring 172 that is formed on the outer surface of the inner tubular body 154. The dimensions of the inner surface of the groove 170 can be approximately equal to those of the outer surface of the annular ring 172. In some configurations, the annular ring 172 can rotate within the groove 170 to permit the inner tubular body 154 to rotate from a first position to a second position. Furthermore, the combination of the groove 170 and the annular ring 172 can interlock the inner tubular body 154 within the outer tubular body 152 to maintain the two together.

FIGS. 13-14 depict a septum activator 150 within a catheter assembly 10. Similar to the septum activators 80, 111 of FIGS. 3-5 and 9-10, the septum activator 150 can be configured to be compatibly inserted into the cavity 54 within the proximal side of the septum 50 so that it is positioned where it can pierce through the slit 56 of the barrier member 52 to form a fluid path therethrough. The distal end includes a leading surface that can be inserted through the septum 50 to a position proximal to the barrier member 52 of the septum 50, as shown in FIG. 14.

As shown in FIG. 13, when the septum activator 150 is disposed in a deactivated position in the catheter adapter 12, and the inner tubular body 154 is in a first position relative to the outer tubular body 152, the septum activator 150 forms a barrier surface of the flashback chamber 116. Thus, during flashback, fluid can flow along a fluid flow path 180 into the flashback chamber 116. When the tubular body 115 is in a first position relative to the outer tubular body 152, the septum activator can form a fluid-tight barrier that prevents leakage of fluids from the flashback chamber 116 into the inner lumen 88 of the inner tubular body 154. As fluid enters the flashback chamber 116, it provides a clinician with an observable indicator that the catheter 12 is properly placed.

Referring to FIG. 14, once the catheter 12 is properly placed, a conduit coupler 42 can connect an intravenous tubing 40 to the catheter adapter 14 to begin infusing fluid into the patient. As the conduit coupler 42 is inserted onto the catheter adapter 14, the probe member 46 enters into the inner lumen 36 of the catheter adapter and contacts the contact surface 132 of the inner tubular body 154. When the probe member 46 is completely advanced, the septum activator 150 pierces the septum 50. Once fully inserted, the conduit coupler 41 can be fastened to the catheter adapter 14. As mentioned, this connection can be between threads on both the conduit coupler 42 and the catheter adapter 14.

The action of rotating the conduit coupler 42 (in a direction represented by arrow 168) to connect it to the catheter adapter 14 can rotate the inner tubular body 154 from a first position to a second position, wherein openings 158, 160 in the inner tubular body 154 overlap openings 160, 166 in the outer tubular body. As this point, one or more fluid paths 184, 188 are open between the inner lumen 88 of the inner tubular body 154 and the flashback chamber 116.

In some configurations, the friction between the probe member 46 and the septum activator enables the movement of the inner tubular body 154 from a first position to a second position. In some embodiments, the friction coefficient between the contact surface 132 of the septum activator 150 and the leading surface 170 of the probe member 46 provides enough friction to transfer the rotational movement of the probe member 46 to the inner tubular body 154. In other embodiments, the probe member 46 does not contact the contact surface 132, but is inserted into the inner lumen 88 of the inner tubular body 154 and the outer surface of the probe member contacts the inner surface of the inner tubular body 154. In some embodiments, the friction coefficient between the outer surface of the probe member 46 and the inner surface of the inner tubular body 154 is enough to transfer the rotational movement of the probe member 46 to the inner tubular body 154. Accordingly, in some embodiments, the contact surface 132, the leading surface 170, the probe member 46, or the inner surface of the inner tubular body 154 includes a gripping feature that provides sufficient friction to reduce or eliminate slipping between the septum activator 150 and the probe member 46. The gripping feature can include a tacky material, a rough surface, or the like.

After the septum activator 150 activates the septum 50 and the inner tubular member 154 is in a second position in relation to the outer tubular body 152, fluid can be infused into the catheter assembly 10. Fluid entering the catheter assembly 10 can flow along one or more fluid flow paths 184, 186, 188 in and out of the overlapping openings of the septum activator 150, through the inner lumen 88 of the inner tubular body 154, and through the flow restrictors 70 between the septum 50 and the catheter adapter 14. In this manner, fluid within the flashback chamber 116 can be flushed out the catheter assembly 10.

From the foregoing, it can be seen that a pierced septum valve can provide selective activation of fluid flow through the catheter assembly while minimizing or eliminating blood exposure. The pierced septum valve can enhance a clinician's ability to confirm catheter placement by providing an additional flashback chamber between a seal around the exterior of the septum activator and the septum. Additionally, the septum activator can provide selective openings therein that open during activation and close when the septum activator is in a deactivated position. When closed, the openings form a barrier surface of the additional flashback chamber. When open, the openings provided fluid pathways through the septum activator that can flush fluid contained in the additional flashback chamber about the septum activator.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A septum activator comprising:
   an outer tubular body having a plurality of openings therein;
   an inner tubular body disposed within the outer tubular body and having a plurality of openings therein, the inner tubular body having a first position relative to the outer tubular body and a second position relative to outer tubular body;
   wherein in the first position, the plurality of openings of the inner tubular body do not overlap with the plurality of openings in the outer tubular body;
   wherein in the second position, the plurality of openings of the inner tubular body overlap with the plurality of openings of the outer tubular body;
   a seal disposed on an outer surface of the septum activator; and
   one or more vents disposed on the seal, the one or more vents each permit the passage of air but not blood.

2. The septum activator of claim 1, wherein the inner tubular body moves from the first position to the second position as the inner tubular body or outer tubular body is rotated about a longitudinal axis of the inner body.

3. The septum activator of claim 1, wherein the inner tubular body moves from the first position to the second position as the inner tubular body or the outer tubular body is translated along a longitudinal axis of the inner body.

4. The septum activator of claim 1, wherein the plurality of openings in the outer tubular body includes a plurality of openings in a proximal portion of the outer tubular body and a plurality of openings in a distal portion of the outer tubular body; and wherein the plurality of openings in the inner tubular body includes a plurality of openings in a proximal portion of the inner tubular body and a plurality of openings in a distal portion of the inner tubular body.

5. The septum activator of claim 4, wherein the inner tubular body and the outer tubular body each have a tapered portion.

6. The septum activator of claim 1, wherein each of the one or more vents has cross sectional area of less than or equal to 0.00003 inches$^2$.

7. The septum activator of claim 1, further comprising one or more interlocking features between the inner tubular body and the outer tubular body that retain the inner tubular body within the outer tubular body.

8. A catheter assembly comprising:
   a catheter adapter having a lumen extending therethrough;
   a septum disposed within the lumen;
   a septum activator disposed within the lumen proximal the septum, the septum activator having an inner tubular body and an outer tubular body, the outer tubular body of the septum activator having a plurality of openings therein, the inner tubular body of the septum activator disposed within the outer tubular body and having a plurality of openings therein, the inner tubular body having a first position relative to the outer tubular body and a second position relative to outer tubular body;
   wherein in the first position, the plurality of openings of the inner tubular body do not overlap with the plurality of openings in the outer tubular body; and
   wherein in the second position, the plurality of openings of the inner tubular body overlap the plurality of openings of the outer tubular body.

9. The catheter assembly of claim 8, wherein the inner tubular body moves from the first position to the second position as the inner tubular body or outer tubular body is rotated about a longitudinal axis of the inner body.

10. The catheter assembly of claim 8, wherein the inner tubular body moves from the first position to the second position as the inner tubular body or the outer tubular body is translated along a longitudinal axis of the inner body.

11. The catheter assembly of claim 8, wherein the plurality of openings in the outer tubular body includes a plurality of openings in a proximal portion of the outer tubular body and a plurality of openings in a distal portion of the outer tubular body; and wherein the plurality of openings in the inner tubular body includes a plurality of openings in a proximal portion of the inner tubular body and a plurality of openings in a distal portion of the inner tubular body.

12. The catheter assembly of claim 11, wherein the inner tubular body and the outer tubular body each has a tapered portion.

13. The catheter assembly of claim 8, further comprising a seal disposed between an outer surface of the septum activator and the catheter adapter, the seal sealing the portion of the septum activator distal the lumen from the portion of the septum activator proximal the lumen.

14. The catheter assembly of claim 13, further comprising one or more flow restrictors disposed on the seal, the one or more flow restrictors having cross sectional areas less than or equal to 0.00003 inches$^2$.

15. The catheter assembly of claim 8, further comprising one or more interlocking features between the inner tubular body and the outer tubular body that retain the inner tubular body within the outer tubular body.

16. The catheter assembly of claim 8, wherein the volume exterior the septum activator between the septum and the seal form a flashback chamber.

17. The catheter assembly of claim 16, wherein when the inner tubular body is in the second position the inner tubular body and the outer tubular body form a fluid tight barrier between an inner lumen of the inner tubular body and the flashback chamber.

18. The catheter assembly of claim 8, further comprising one or more flow restrictors between the septum and an inner surface of the catheter adapter, the one or more flow restrictors each having cross sectional areas greater than 0.00003 inches$^2$.

19. A catheter assembly comprising:
   a catheter adapter having a lumen extending therethrough;
   a septum disposed within the lumen;
   a septum activator disposed within the lumen proximal the septum, the septum activator having an inner tubular body and an outer tubular body, the outer tubular body of the septum activator having a plurality of openings therein, the inner tubular body of the septum activator disposed within the outer tubular body and having a plurality of openings therein, the inner tubular body having a first position relative to the outer tubular body and a second position relative to outer tubular body;
   wherein in the first position the plurality of openings of the inner tubular body do not overlap with the plurality of openings in the outer tubular body;
   wherein in the second relative position the plurality of openings of the inner tubular body overlap the plurality of openings of the outer tubular body;
   an annular seal disposed between an outer surface of the septum activator and an inner surface of the lumen, the seal being disposed about a proximal portion of the septum activator; and
   one or more vents disposed between the seal and the lumen of the body.

* * * * *